United States Patent
Oxborough

(10) Patent No.: US 11,585,759 B2
(45) Date of Patent: Feb. 21, 2023

(54) COUNTING PHOTOACTIVE CELLS

(71) Applicant: Chelsea Technologies Ltd, West Molesey (GB)

(72) Inventor: Kevin Oxborough, West Molesey (GB)

(73) Assignee: CHELSEA TECHNOLOGIES LTD, West Molesey (GB)

( * ) Notice: Subject to any disclaimer, the term of this patent is extended or adjusted under 35 U.S.C. 154(b) by 1075 days.

(21) Appl. No.: 16/317,612

(22) PCT Filed: Jul. 10, 2017

(86) PCT No.: PCT/GB2017/052020
§ 371 (c)(1),
(2) Date: Jan. 14, 2019

(87) PCT Pub. No.: WO2018/011554
PCT Pub. Date: Jan. 18, 2018

(65) Prior Publication Data
US 2019/0242825 A1 Aug. 8, 2019

(30) Foreign Application Priority Data

Jul. 15, 2016 (GB) ...................................... 1612336

(51) Int. Cl.
*G01N 21/64* (2006.01)
*G01N 33/18* (2006.01)
(Continued)

(52) U.S. Cl.
CPC ....... *G01N 21/6486* (2013.01); *C12M 1/3446* (2013.01); *G01N 15/06* (2013.01);
(Continued)

(58) Field of Classification Search
CPC ............... G01N 21/6486; G01N 15/06; G01N 21/6408; G01N 21/85; G01N 33/1826;
(Continued)

(56) References Cited

U.S. PATENT DOCUMENTS 8,820,538 B1 * 9/2014 Lin .................... B01L 3/502753
209/552
2012/0208264 A1 8/2012 Bernd et al.
2015/0211043 A1 7/2015 Ram et al.

FOREIGN PATENT DOCUMENTS

DE 199 30 865 A1 2/2001
EP 2 889 365 A1 7/2015
(Continued)

OTHER PUBLICATIONS

Gollasch et al. "Quantifying indicatively living phytoplankton cells in ballast water samples—recommendations for Port State Control", Marine Pollution Bulletin 101, 2015, 768-775 (Year: 2015).*

(Continued)

*Primary Examiner* — Samuel P Siefke
*Assistant Examiner* — Henry H Nguyen
(74) *Attorney, Agent, or Firm* — Scully, Scott, Murphy & Presser, P.C.

(57) ABSTRACT

Cell counting device A cell counting device and a method of using a cell counting device are disclosed. The cell counting device comprises a chamber for receiving a sample, at least one light source to emit light towards a section of the chamber. The section of the chamber comprises a sub-sample of the sample. The cell counting device also comprises a light detector to receive a light emitted from the section of the chamber and to generate an electronic signal associated with the received light, and a controller. The controller is configured to estimate the number of photoactive cells in the sample by calculating the distribution of variable fluorescence [$F_v$] values of a predetermined number of sub-samples about the mean $F_v$ value.

12 Claims, 15 Drawing Sheets

(51) Int. Cl.
   *G01N 21/85*    (2006.01)
   *G01N 15/06*    (2006.01)
   *C12M 1/34*     (2006.01)
   *G01N 21/63*    (2006.01)
   *G01N 15/00*    (2006.01)
   *C12Q 1/06*     (2006.01)
   *C02F 103/00*   (2006.01)
   *B63J 4/00*     (2006.01)

(52) U.S. Cl.
   CPC ........ *G01N 21/6408* (2013.01); *G01N 21/85* (2013.01); *G01N 33/1826* (2013.01); *G01N 33/1893* (2013.01); *B63J 4/002* (2013.01); *C02F 2103/008* (2013.01); *C02F 2209/36* (2013.01); *C12Q 1/06* (2013.01); *G01N 2015/0065* (2013.01); *G01N 2015/0687* (2013.01); *G01N 2015/0693* (2013.01); *G01N 2021/635* (2013.01); *G01N 2201/0696* (2013.01)

(58) Field of Classification Search
   CPC ....... G01N 33/1893; G01N 2015/0065; G01N 2015/0687; G01N 2015/0693; G01N 2021/635; G01N 2201/0696; C12M 1/3446; B63J 4/002; C02F 2103/008; C02F 2209/36; C12Q 1/06
   See application file for complete search history.

(56) References Cited

FOREIGN PATENT DOCUMENTS

JP    2013-50375 A     3/2013
WO    2016-071356 A1   5/2016

OTHER PUBLICATIONS

Briski et al., "Evaluating efficacy of a ballast water filtration system for reducing spread of aquatic species in freshwater ecosystems", Management of Biological Invasions, 2014, 5, 3, 245-253 (Year: 2014).*

Jakob T. et al., "Estimation of Chlorophyll Content and Daily Primary Production of the Major Algal Groups by Means of Multiwavelength-Excitation PAM Chlorophyll Fluorometry: Performance and Methodological Limits", Photosynthesis Research 83(1):343-361 (Mar. 1, 2005).

Parésys G. et al., "Quantitative and Qualitative Evaluation of Phytoplankton Communities by Trichromatic Chlorophyll Fluorescence Excitation With Special Focus on Cyanobacteria", 39:911-921 (2005).

Popp P W, "Phytoplankton Analyzer PHYTO-PAM and Phyto-Win Software V 1.45—System Components and Principles of Operation", Heinz Walz GmbH, pages Front p. 127 (Jul. 1, 2003).

International Search Report and Written Opinion dated Oct. 5, 2017 received in International Application No. PCT/GB2017/052020.

* cited by examiner

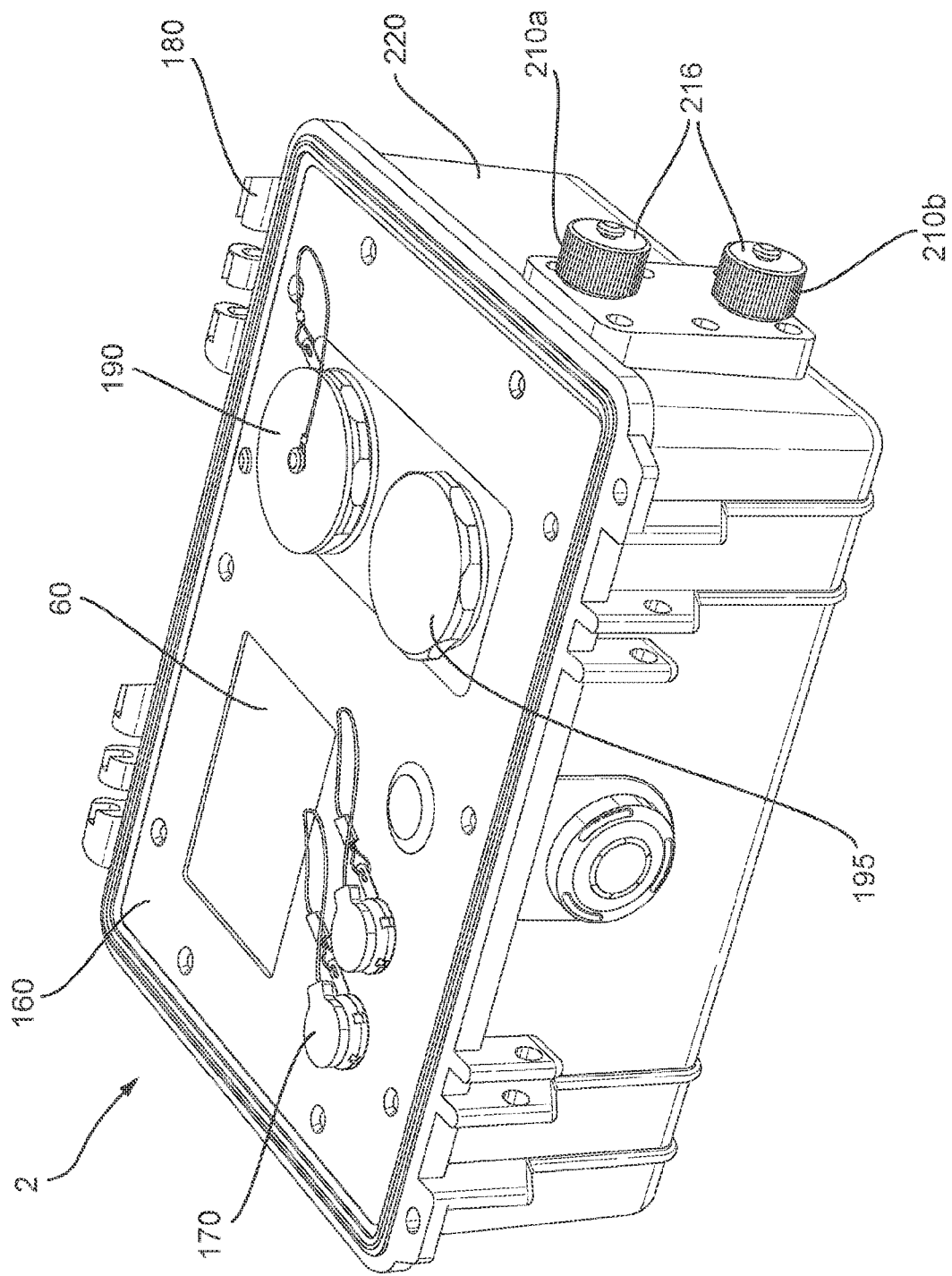

COUNTING PHOTOACTIVE CELLS

FIELD

The present invention relates to cell counting devices, and in particular to the use of such devices for detecting and counting live phytoplankton cells in ballast water. More specifically, the invention relates to a method and cell counting device for counting photoactive cells.

BACKGROUND

The international maritime industry, with more than 70,000 merchant vessels, is responsible for transporting more than 80% of the goods traded in world markets. Accordingly, it can be viewed as a foundation of the global economy. However, commercial shipping requires the use of ballast water, which is taken up when cargo is unloaded and discharged when cargo is loaded. The ballast water can contain marine life. Accordingly, when the water is discharged it can result in the introduction of aquatic invasive species to coastal waters where they can cause enormous ecological and economic damage.

The International Maritime Organization's (IMO) International Convention for the Control and Management of Ships' Ballast Water and Sediments, adopted in 2004 but not yet ratified or entered into force, includes a discharge standard to reduce the transport and delivery of potential Aquatic Nuisance Species. Concurrently in the United States, the U.S. Coast Guard (USCG) developed and finalized ballast water discharge standards (BWDSs) that limit concentrations of living organisms that can be released with ballast water and new regulations that require ship operators to meet those limits. The USCG discharge standard, which is the same as that of the IMO, will begin to apply to ships constructed on or after Dec. 1, 2013 and for ships constructed prior to that date in 2014 or 2016, depending on ballast water capacity.

To address the IMO and U.S. discharge standards, technology developers and manufacturers around the world have designed and built a variety of on-board ballast water treatment systems (BWTS) to achieve the prescribed discharge limits. To date, several dozen BWTS have been tested by independent laboratories and have received type approval certifications from various international administrations in accordance with the IMO convention. These systems include treatment processes such as: de-oxygenation, filtration, ultraviolet radiation, ozonation, and various chemical treatments, including electro-catalytic chlorination, peracetic acid, hydrogen peroxide, perchloric acid, and chlorine dioxide.

The BWDSs limit the cell concentration within a ballast water sample to 10 live phytoplankton cells per mL, for cells greater than or equal to 10 µm and less than 50 µm in the smallest dimension. This value can be associated with a variable fluorescence which is set as a threshold, and a sample is said to pass or fail the test according to whether or not its variable fluorescence exceeds this threshold. However, variable fluorescence per cell varies by more than a factor of 100, and so the variable fluorescence of the sample cannot be used to accurately determine the number of live phytoplankton cells within a sample (or, in other words, the cell concentration).

At present, known technologies generate a pass or fail result based only on the measured variable fluorescence, as required by the BWDSs. In other words, known technologies may fail a sample that emits a large variable fluorescence, because this gives the impression of a high cell density, but in reality the sample may contain only a few cells that happen to be highly emissive (such as *Thalassiosira punctigera*). This is a false positive result.

It follows that there are currently no commercially available technologies to reliably monitor the density (or cell concentration) of live phytoplankton cells within ballast water, in real-time.

It would be readily apparent that the same problem of not being able to accurately determine cell density, and consequently cell count for a known sample volume, would be relevant to other fields such as experiments involving cell cultures and assays, or in testing waterways.

Aspects of the present invention aim to address one or more drawbacks inherent in prior art methods and apparatus for detecting photoactive cells, particularly in ballast water.

SUMMARY

According to a first aspect of the present invention, there is provided a cell counting device for estimating the number of photoactive cells in a sample, the device comprising:
 a chamber for receiving a sample;
 at least one light source to generate at least one pulse of light and to emit the at least one pulse of light towards a section of the chamber, wherein the section of the chamber comprises a sub-sample of the sample;
 a light detector to receive light emitted from the sub-sample in response to receiving the at least one pulse of light and to generate an electronic signal associated with the received light; and
 a controller configured to:
  estimate the number of photoactive cells in the sample by calculating the distribution of variable fluorescence $[F_v]$ values of a predetermined number of sub-samples about the mean $F_v$ value.

Advantageously, the device of the first aspect provides a means for accurately estimating the number of photoactive cells in a sample. Further advantages are set out in the detailed description that follows.

Preferably, the at least one light source is configured to generate a plurality of pulses of light, and the light detector is configured to receive light from the sub-sample at time intervals less than the duration of each pulse of light to form a light signal. The at least one light source is configured to generate pulses of light having a frequency of preferably between 10 Hz and 100 Hz, more preferably between 20 Hz and 80 Hz, and most preferably between 30 Hz and 60 Hz. The frequency is preferably less than 50 Hz. The at least one light source is configured to generate pulses of light having a duration of preferably between 200 µs and 700 µs, more preferably between 300 µs and 600 µs, and most preferably between 350 µs and 450 µs. The duration is preferably less than 500 µs. The duration is preferably more than 300 µs. In an exemplary embodiment, the at least one light source is configured to generate pulses of light having a duration of 400 µs and a frequency of 40 Hz.

Calculating the distribution preferably comprises the controller being configured to calculate and store the $F_v$ value of each sub-sample in the predetermined number of sub-samples.

Preferably, the controller is be configured to calculate the $F_v$ value of a sub-sample by estimating a minimal fluorescence $[F_o]$ of the sub-sample using regression analysis of a first part of the light signal, estimating a maximal fluorescence $[F_m]$ of the sub-sample using regression analysis of a second part of the light signal, and subtracting $F_o$ from $F_m$.

If an $F_v$ value for each of the predetermined number of sub-samples is stored, the controller is preferably configured to calculate the mean of the stored $F_v$ values, and store the distribution of distance from the mean of each $F_v$ value.

Preferably, the controller is configured to integrate the distribution to provide an estimate of the number of cells within the sample.

Preferably, the controller is configured to estimate the cell density of the sample by dividing the estimate of the number of cells by the volume of the sample.

Preferably, the controller is configured to perform an action if the estimated cell density is greater than a first cell density threshold. More preferably, the cell counting device further comprises a means for indicating to the user that the estimated cell density exceeds the first cell density threshold, and the action comprises activating the indicating means. Even more preferably, the indicating means comprises at least one of a display, an alarm and an indicator light. Alternatively, the cell counting device is coupled to an external display device, and the controller is configured to perform an action comprising controlling the external display device to display a message. Alternatively again, the cell counting device is coupled to a ballast water treatment system, and the controller is configured to perform an action comprising controlling the ballast water treatment system to eliminate live cells.

Preferably, the cell counting device further comprises an outlet in fluid communication with the chamber for draining the sample from the chamber. More preferably, the cell counting device further comprises an inlet in fluid communication with the chamber, arranged such that water can continuously flow from the inlet, through the chamber, to the outlet in a first mode of operation. Even more preferably, the chamber comprises a removable blocking member for blocking the inlet or the outlet to allow a discrete sample to be measured in a second mode of operation.

Preferably, the cell counting device further comprises a stirrer configured to stir the sample, such that each sub-sample is exchanged with the sample. More preferably, the stirrer is arranged to pass through a side wall of the chamber. Alternatively, the blocking member comprises the stirrer.

Preferably, the cell counting device further comprises a valve arranged in at least one of the inlet or the outlet operable to allow the cell counting device to alternate between the first mode of operation and the second mode of operation, wherein in the first mode of operation the valve is open, and in the second mode of operation the valve is closed. The cell counting device may first measure a sample in continuous-flow mode, and then switch to discrete-sample mode to take a more accurate measurement. The cell counting device may then continue in stop-flow mode so as to alternate between continuous-flow mode and discrete-sample mode at regular intervals. Here, the first mode of operation is the continuous-flow mode and the second mode of operation is the discrete-sample mode.

Preferably, the controller is configured to calculate the variable fluorescence of a sub-sample while the cell counting device operates in the first mode of operation, and if the variable fluorescence is less than a first $F_v$ threshold and is greater than a second $F_v$ threshold being less than the first $F_v$ threshold, the valve is closed and the cell counting device is configured to switch to operate in the second mode of operation.

Alternatively or additionally, if the estimated cell density exceeds a second cell density threshold less than the first cell density threshold, the cell counting device is arranged to switch to the first mode of operation from the second mode of operation at an increased frequency.

Preferably, the cells are biological fluorophores. More preferably, the sample is ballast water, and the cells are preferably phytoplankton. Alternatively, the cells comprise a photoactive organic dye.

Preferably, the volume of each sub-sample is between 0.5% and 50% of the sample volume. More preferably, the volume of each sub-sample is between 1% and 20% of the sample volume. Most preferably, the volume of each sub-sample is between 2% and 5% of the sample volume. In an exemplary embodiment, the volume of each sub-sample is 2.5% of the sample volume.

The sample may comprise cells of different sizes, and the controller is preferably further configured to calculate an average $F_v$ per cell for the cells contributing to the distribution. More preferably, the controller is further configured to estimate the $F_v$ attributable to the cells that contribute to the distribution. More preferably, the controller is further configured to subtract the $F_v$ attributable to the cells that contribute to the distribution from the total $F_v$ to estimate the $F_v$ attributable to cells having a threshold $F_v$ per cell that is too small to contribute to the distribution. The threshold $F_v$ per cell is preferably about 5% of the average $F_v$ for the cells that do contribute to the distribution.

According to a second aspect of the present invention, there is provided a system comprising:
 a ballast water treatment system; and
 the cell counting device according to the first aspect, wherein the cell counting device is configured to control the ballast water treatment system to activate a means for eliminating live cells if the estimated cell density exceeds a cell density threshold.

According to a third aspect of the present invention, there is provided a system comprising:
 a measurement device comprising:
  a chamber for receiving a sample;
  at least one light source to generate at least one pulse of light and emit the at least one pulse of light towards a section of the chamber, wherein the section of the chamber comprises a sub-sample of the sample; and
  a light detector to receive light emitted from the sub-sample in response to receiving the at least one pulse of light and to generate an electronic signal associated with the received light;
  an interface for electronically coupling the device to a computing device; and
 a computing device comprising:
  an interface for electronically coupling the computing device to the measurement device such that the computing device receives an electronic signal associated with the received light; and
  a controller configured to estimate the number of photoactive cells in the sample by calculating the distribution of variable fluorescence [$F_v$] values of a predetermined number of sub-samples about the mean $F_v$ value.

Preferably, the at least one light source is configured to generate a plurality of pulses of light, and the light detector is configured to receive light from the sub-sample at time intervals less than the duration of each pulse of light to form a light signal. The at least one light source is configured to generate pulses of light having a frequency of preferably between 10 Hz and 100 Hz, more preferably between 20 Hz and 80 Hz, and most preferably between 30 Hz and 60 Hz. The frequency is preferably less than 50 Hz. The at least one light source is configured to generate pulses of light having a duration of preferably between 200 μs and 700 μs, more preferably between 300 μs and 600 μs, and most preferably between 350 μs and 450 μs. The duration is preferably less than 500 μs. The duration is preferably more than 300 μs. In an exemplary embodiment, the at least one light source is configured to generate pulses of light having a duration of 400 μs and a frequency of 40 Hz.

Preferably, calculating the distribution comprises the controller being configured to calculate and store the $F_v$ value of each sub-sample in the predetermined number of sub-samples.

Preferably, the controller is configured to calculate the $F_v$ value of a sub-sample by estimating a minimal fluorescence $[F_o]$ of the sub-sample using regression analysis of a first part of the received light signal, estimating a maximal fluorescence $[F_m]$ of the sub-sample using regression analysis of a second part of the received light signal, and subtracting $F_o$ from $F_m$.

Preferably, if an $F_v$ value for each of the predetermined number of sub-samples is stored, the controller is configured to calculate the mean of the stored $F_v$ values, and store the distribution of distance from the mean of each $F_v$ value. Even more preferably, the controller is configured to integrate the distribution to provide an estimate of the number of cells within the sample.

Preferably, the controller is configured to estimate the cell density of the sample by dividing the estimate of the number of cells by the volume of the sample.

Preferably, the controller is configured to perform an action if the estimated cell density is greater than a first cell density threshold.

Preferably, the system further comprises a means for indicating to the user that the estimated cell density exceeds the first cell density threshold, wherein the action comprises controlling the indicating means. More preferably, the indicating means comprises at least one of a display on the measurement device, a display on the computing device, an alarm and an indicator light. Alternatively, the system further comprises a ballast water treatment system, and performing an action comprises controlling the ballast water treatment system to eliminate live cells.

Preferably, the measurement device further comprises an outlet in fluid communication with the chamber for draining the sample from the chamber. More preferably, the measurement device further comprises an inlet in fluid communication with the chamber, arranged such that water can continuously flow from the inlet, through the chamber, to the outlet in a first mode of operation.

Preferably, the chamber comprises a removable blocking member for blocking the inlet or the outlet to allow a discrete sample to be measured in a second mode of operation.

Preferably, the measurement device further comprises a valve arranged in at least one of the inlet or the outlet operable to allow the measurement device to alternate between the first mode of operation and the second mode of operation, wherein in the first mode of operation the valve is open, and in the second mode of operation the valve is closed.

Preferably, the controller is configured to calculate the variable fluorescence of a sub-sample while the measurement device operates in the first mode of operation, and if the variable fluorescence is less than a first $F_v$ threshold and is greater than a second $F_v$ threshold being less than the first $F_v$ threshold, the valve is closed and the measurement device is configured to switch to operate in the second mode of operation.

Preferably, if the estimated cell density exceeds a second cell density threshold less than the first cell density threshold, the measurement device is arranged to switch to the first mode of operation from the second mode of operation at an increased frequency.

Preferably, the system further comprises a stirrer configured to stir the sample, such that each sub-sample is exchanged with the sample. More preferably, the stirrer is arranged to pass through a side wall of the chamber. Alternatively, the blocking member comprises the stirrer.

Preferably, the cells are biological fluorophores. More preferably, the sample is ballast water, and the cells are preferably phytoplankton. Alternatively, the cells comprise a photoactive organic dye.

Preferably, the volume of each sub-sample is between 0.5% and 50% of the sample volume. More preferably, the volume of each sub-sample is between 1% and 20% of the sample volume. Most preferably, the volume of each sub-sample is between 2% and 5% of the sample volume. In an exemplary embodiment, the volume of each sub-sample is 2.5% of the sample volume.

The sample may comprise cells of different sizes, and the controller is preferably configured to calculate an average $F_v$ per cell for the cells contributing to the distribution. More preferably, the controller is further configured to estimate the $F_v$ attributable to the cells that contribute to the distribution. More preferably, the controller is further configured to subtract the $F_v$ attributable to the cells that contribute to the distribution from the total $F_v$ to estimate the $F_v$ attributable to cells having a threshold $F_v$ per cell that is too small to contribute to the distribution. The threshold $F_v$ per cell is preferably about 5% of the average $F_v$ for the cells that do contribute to the distribution.

According to a fourth aspect of the present invention, there is provided a method of counting cells, comprising:
for a predetermined number of sub-samples of a sample:
  generating at least one pulse of light and directing it towards one of the predetermined number of sub-samples; and
  receiving a light emitted from the sub-sample in response to receiving the at least one pulse of light and generating an electronic signal associated with the received light; and the method further comprising:
  estimating the number of photoactive cells in the sample by calculating the distribution of variable fluorescence $[F_v]$ values of the plurality of sub-samples about the mean $F_v$ value.

The method preferably comprises generating a plurality of pulses of light, and receiving light from the sub-sample at time intervals less than the duration of each pulse of light to form a light signal. Preferably, the method comprises generating pulses of light having a frequency of preferably between 10 Hz and 100 Hz, more preferably between 20 Hz and 80 Hz, and most preferably between 30 Hz and 60 Hz. The frequency is preferably less than 50 Hz. Preferably, the method comprises generating pulses of light having a duration of preferably between 200 μs and 700 μs, more preferably between 300 μs and 600 μs, and most preferably between 350 μs and 450 μs. The duration is preferably less than 500 μs. The duration is preferably more than 300 μs. In an exemplary embodiment, the method comprises generating pulses of light having a duration of 400 μs and a frequency of 40 Hz.

Preferably, calculating the distribution comprises calculating and storing the $F_v$ value of each sub-sample in the predetermined number of sub-samples.

Preferably, calculating an $F_v$ value of a sub-sample comprises estimating a minimal fluorescence [$F_o$] of the sub-sample using regression analysis of a first part of the light signal, estimating a maximal fluorescence [$F_m$] of the sub-sample using regression analysis of a second part of the light signal, and subtracting $F_o$ from $F_m$.

If an $F_v$ value for each of the predetermined number of sub-samples has been stored, calculating the distribution preferably comprises calculating the mean of the stored $F_v$ values, and storing the distribution of distance from the mean of each $F_v$ value.

Preferably, the method comprises integrating the distribution to provide an estimate of the number of cells within the sample.

Preferably, the method further comprises estimating the cell density of the sample by dividing the estimate of the number of cells by the volume of the sample.

Preferably, the method further comprises performing an action if the estimated cell density exceeds a first cell density threshold. More preferably, performing the action comprises indicating that the estimated cell density exceeds the first cell density threshold. Even more preferably, indicating that the estimated cell density exceeds the first cell density threshold comprises at least one of controlling a display to display a message, activating an alarm, or activating an indicator light. Alternatively, performing the action comprises controlling a means for exterminating live cells.

Preferably, the method further comprises stirring the sample if the number of stored $F_v$ values is less than the predetermined number of sub-samples.

Preferably, the method comprises receiving the sample while operating the cell counting device in a continuous-flow mode, stopping the continuous flow of sample, and performing the method as previously described while operating the cell counting device in a discrete-sample mode. More preferably, the method further comprises operating the cell counting device in a continuous-flow mode, and calculating the variable fluorescence of the sub-sample, wherein if the variable fluorescence of a sub-sample is less than a first $F_v$ threshold and is greater than a second $F_v$ threshold being less than the first $F_v$ threshold, the method comprises stopping the continuous-flow mode and performing the method as previously described while operating the cell counting device in a discrete-sample mode.

The method alternatively or additionally further comprises reducing the time period between receiving the sample and stopping the continuous flow of sample if the estimated cell density exceeds a second cell density threshold less than the first cell density threshold.

Preferably, the cells are biological fluorophores. More preferably, the sample is ballast water, and the cells are preferably phytoplankton. Alternatively, the method further comprises applying a photoactive organic dye to the cells. The organic dye provides a photoactive response in cells that would not normally fluoresce.

Preferably, the volume of each sub-sample is between 0.5% and 50% of the sample volume. More preferably, the volume of each sub-sample is between 1% and 20% of the sample volume. Most preferably, the volume of each sub-sample is between 2% and 5% of the sample volume. In an exemplary embodiment, the volume of each sub-sample is 2.5% of the sample volume.

The sample may comprise cells of different sizes, and the method preferably further comprises calculating an average $F_v$ per cell for the cells contributing to the distribution. More preferably, the method further comprises estimating the $F_v$ attributable to the cells that contribute to the distribution. More preferably, the method further comprises subtracting the $F_v$ attributable to the cells that contribute to the distribution from the total $F_v$ to estimate the $F_v$ attributable to cells having a threshold $F_v$ per cell that is too small to contribute to the distribution. The threshold $F_v$ per cell is preferably about 5% of the average $F_v$ for the cells that do contribute to the distribution.

All features described herein (including any accompanying claims, abstract and drawings), and/or all of the steps of any method or process so disclosed, may be combined with any of the above aspects in any combination, except combinations where at least some of such features and/or steps are mutually exclusive.

BRIEF DESCRIPTION OF THE FIGURES

Embodiments of the present invention will now be described, by way of example only, with reference to the accompanying drawings, in which:

FIG. 7 shows an external perspective view of one embodiment of the cell counting device;

DETAILED DESCRIPTION

Figure 1:
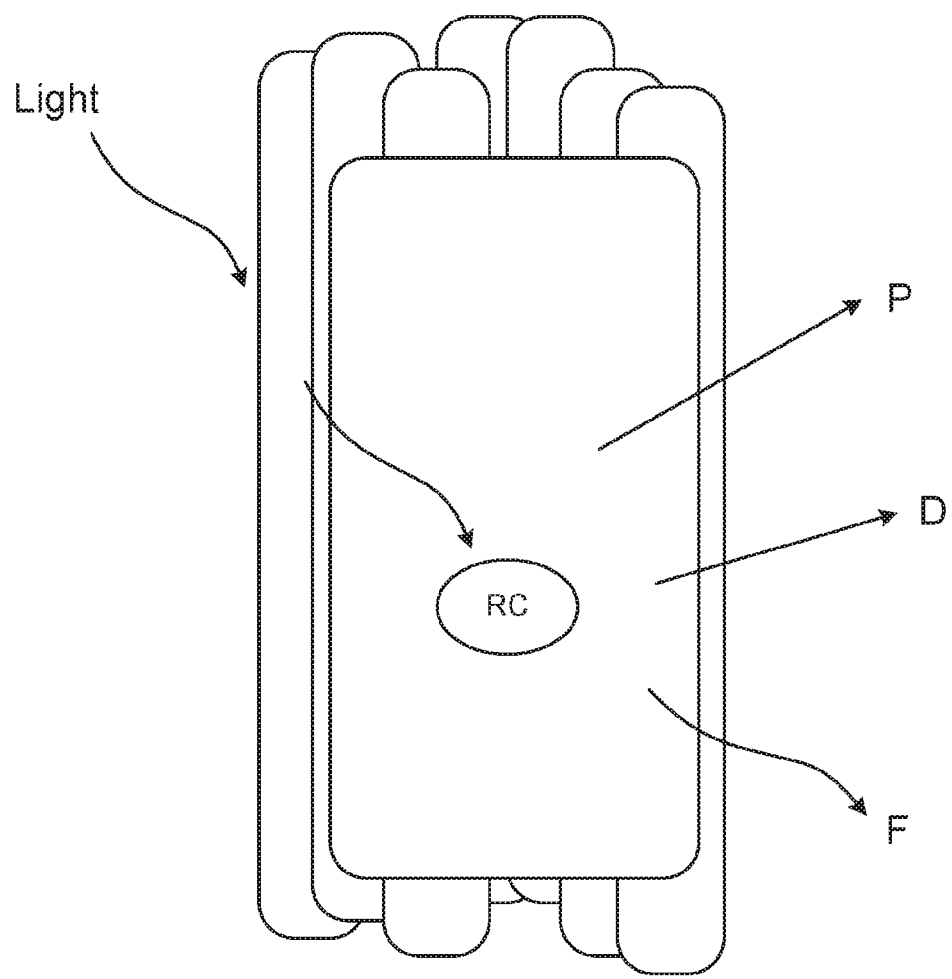
FIG. 1 shows a schematic diagram of a phytoplankton's response to light.

The present invention is concerned with counting live phytoplankton. FIG. 1 shows the processes that occur within phytoplankton, in order to cause detectable fluorescence, although it would be readily understood that the invention that follows can be applied to any type of cell exhibiting a similar response to light as phytoplankton. In the Figure, RC is the Photosystem II Reaction Centre; P is the PSII photochemistry component; D is the non-radiative decay component; and F is the Chlorophyll fluorescence component.

Dead phytoplankton cannot photosynthesise; however, they may emit some detectable fluorescence when exposed to light. The emission from dead phytoplankton is not a time-dependent response. This residual emission is a component of the minimal fluorescence ($F_o$), shown in FIG. 2.

In live phytoplankton, light absorbed by the Light Harvesting Complex is rapidly transferred to a Chlorophyll-a molecule associated with the Reaction Centre RC in Photosystem II (PSII), located in the thylakoid membrane of the phytoplankton. The cycle of photochemistry is then initiated, and a time-dependent florescent response is induced.

Figure 2:
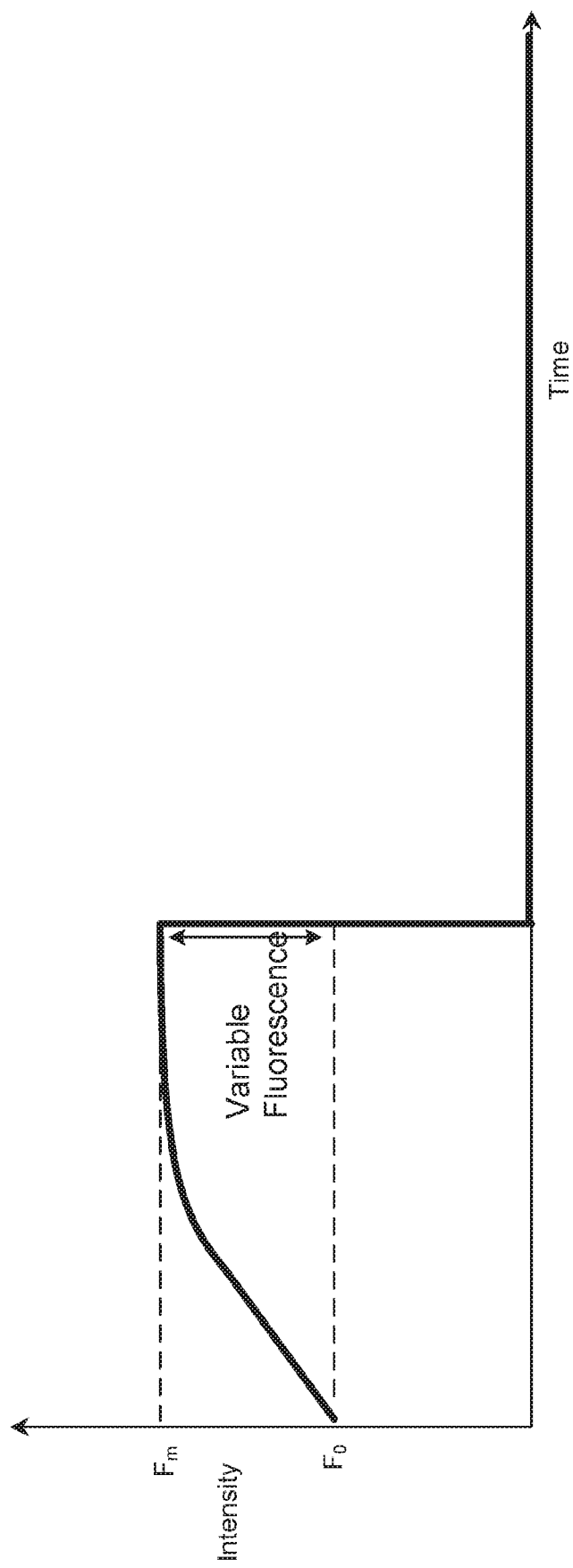
FIG. 2 shows an example of a fluorescence response of a phytoplankton cell.

An example of a typical fluorescent response of phytoplankton is shown in FIG. 2. The objective of prior art devices is to measure the variable fluorescence ($F_v$) of a sample, and use this to pass or fail the sample with regard to the BWDSs. $F_v$ is calculated by measuring the maximal fluorescence ($F_m$) of the sample, and subtracting the minimal fluorescence ($F_o$) from $F_m$. $F_o$ is estimated using linear regression to extrapolate a sequence of 10-20 μs back to time t=0. The skilled person would appreciate that other regression techniques may be used, such as polynomial regression or quantile regression.

However, it has been shown that the $F_v$ value of the sample does not give a realistic estimation of cell count, as will be described with reference to FIG. 9.

While the following described embodiments use a single turnover method, it would be readily apparent that the inventive concept could be implemented on the cell counting device 2 described with reference to FIGS. 3 to 8 using a multiple turnover method. The single turnover refers to the PSII RCs undergoing a single photochemical event during a saturation phase. Consequently, a saturation pulse in the single turnover method is bright enough to saturate PSII photochemistry within 100 to 400 μs. The saturation pulse in the multiple turnover method is less bright and approximately 100 to 1000 times longer than that used in the single turnover method. To achieve saturation, the multiple turnover method relies on multiple photochemical events being induced at each active PSII RC during each saturation pulse.

Figure 3:
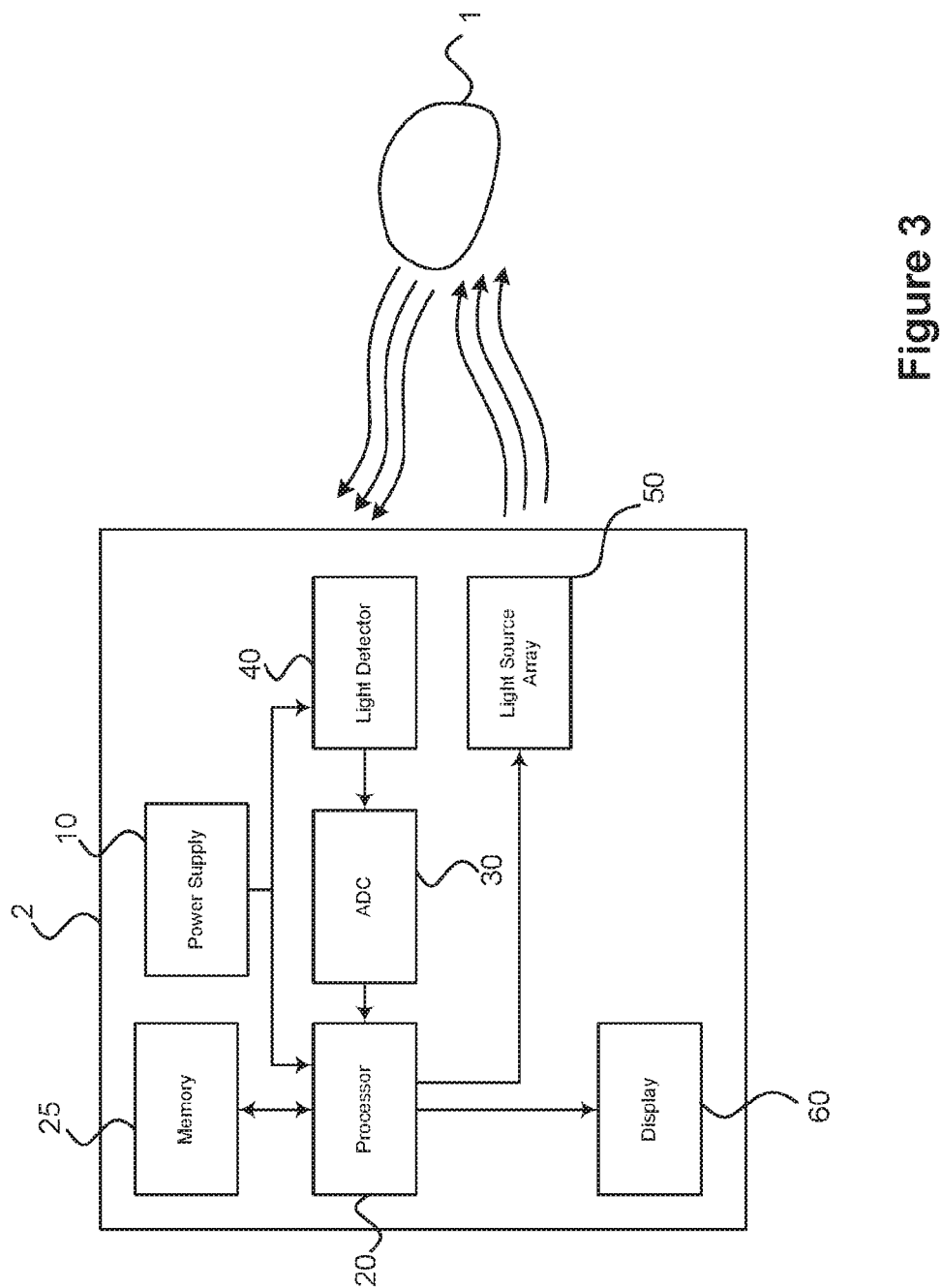
FIG. 3 shows a system diagram of a cell counting device according to an embodiment of the present invention.

With reference to FIG. 3, a cell counting device 2 is shown that includes a light source array 50 and a light detector 40 for measuring the response of a sample 1 to applied photons. For example, the sample 1 is ballast water in the hull of a water-borne vessel, such as a yacht, cargo ship, or submarine, which contains unidentified cells, such as phytoplankton. The cell counting device 2 is configured to determine the number of viable cells within the sample 1, where viable cells are photoactive cells. The viable cells are suspended in the water, and fluoresce when exposed to light of certain wavelengths. Thus, the cell counting device 2 can be used to differentiate between different species of algae present in ballast water of a vessel transiting from region A to region B, and monitor algal populations to assist safeguarding against the unwanted to spread of these invasive species to coastal waters where they can cause ecological and economic damage.

The cell counting device 2 could be integrated with the vessel's ballast water treatment system, or may be a standalone device to test the vessel's internal ballast water monitoring equipment.

The cell counting device 2 includes a power supply 10. The power supply 10 may be, for example, a removable 11.1 V lithium ion battery providing 2.2 Ah. Where the power supply 10 is a battery, an integral charger may be provided so that the battery pack need not be removed from the enclosure in order to be charged. Alternatively, the power supply 10 may be an adapter for coupling the cell counting device 2 to an external power supply. External power is provided from an external 15 V universal input (110-240 VAC) power supply.

The power supply 10 supplies power to the light detector 40. The light detector 40 in an exemplary embodiment is a photomultiplier tube (herein referred to as a PMT). The PMT 40 detects light that is emitted from the sample 1, and applies a gain to the signal so that it can be measured. The PMT 40 may be, for example, a Hamamatsu R9880U-20. Alternatively, the light detector 40 may comprise a photodiode, avalanche photodiode, or multi-pixel photon counter.

The light detector 40 is coupled to an analogue to digital converter (ADC) 30. The ADC converts the signal detected by the light detector 40 into a digital signal that can be interpreted and processed by a processor 20. The processor 20 is configured to use the signal received from the ADC 30 to calculate the variable fluorescence ($F_v$) of the sample 1. This process, and more details about the operation of the processor 20, will be described in more detail later, particularly with reference to FIG. 10.

Although the light detector 40 is shown in FIG. 3 as being separate from the processor 20, other configurations are possible that provide further advantageous effects. For example, in some embodiments, the processor 20 comprises a detector board which includes the PMT 40, a pre-amplifier, PMT high voltage supply and control for the high voltage supply. Ambient overload protection circuitry is incorporated into the detector board. A photodiode is further included for built-in testing and diagnostics.

The processor 20 in an exemplary embodiment is based on the XilinX ZynQ 7000 System on Chip (SoC). The Zynq7 IC features a sophisticated processing and programmable logic core. The processing system (PS) integrates two ARM® Cortex™-A9 MPCore™ application processors, AMBA® interconnect, internal memories, external memory interfaces, and peripherals including USB, Ethernet, SPI, SD/SDIO, I2C, CAN, UART, and GPIO. The PS runs independently of the programmable logic and boots at power-up or reset. The core processor 20 runs a bootloader (u-boot) and embedded Linux operating system from a binary image stored on the SD card. An on-board 2 Mb SDRAM (e.g. H5TQ2G63DFR-RDC) is used by the Linux as a ram drive and system memory.

The cell counting device 2 further includes a display 60. The display 60 may be a resistive touch screen display, such as the eDIPTFT32-A. The processor 20 is configured to control the display 60 using a display driver stored in the memory 25. Alternatively, or in addition to the display 60, the cell counting device 2 may comprise an audible alarm, or an LED indicator.

In some embodiments, which do not require the cell counting device 2 to have a display 60, the cell counting device 2 comprises at least one interface (or in other words, at least one data port) to couple the cell counting device 2 to a computing device such as a tablet or PC. Primary data can be transferred to the computing device via the at least one interface. The computing device may be used to provide full control of the cell counting device 2 and/or display primary data generated by the cell counting device 2. The at least one interface may include a USB interface, Bluetooth interface, an Ethernet interface, or a combination thereof. The skilled person would appreciate that these are exemplary examples of interfaces, and the ballast water monitoring device 2 may include any suitable wired or wireless means for coupling to an external computing device. A graphical user interface (GUI) operating on the computer provides more advanced control and operation of the instrument via the Ethernet interface, USB interface or both. The GUI also allows the instrument configuration and code to be maintained. The ballast water monitoring device 2 having the interface is not limited to embodiments not having a display 60.

The power supply 10 supplies power to the processor 20. The processor 20 is configured to control the light source array 50 using a light source array driver stored in a memory 25. Alternatively, the light source array 50 may be controlled by an LED-on-chip module on the processor 20. The function of the light source array driver is to provide highly reproducible current pulses, of software-controllable amplitude and duration.

In use, the light source array 50 provides pulses of light, each lasting between 200 and 500 μs, at between 10 and 50 Hz. In an exemplary embodiment, the light source array 50 is pulsed for 400 μs at 40 Hz. The 40 data sequences generated each second under this regime are averaged and the resulting sequence of 600 data points (150 pre-pulse points, 400 pulse points and 50 post-pulse points) are exported to the connected computing device. This level of signal averaging provides a high signal to noise ratio, even at very low cell densities. The 150 pre-pulse and 50 post-pulse data points are used to define a signal baseline. The 400 pulse points are analysed in such a way as to determine the level of variable chlorophyll fluorescence ($F_v$) from the sample.

The light source array 50 may be a single light source. Alternatively, the light source array 50 may comprise a plurality of light sources. The light source array 50 according to an exemplary embodiment will now be described with reference to FIG. 4.

Figure 4:
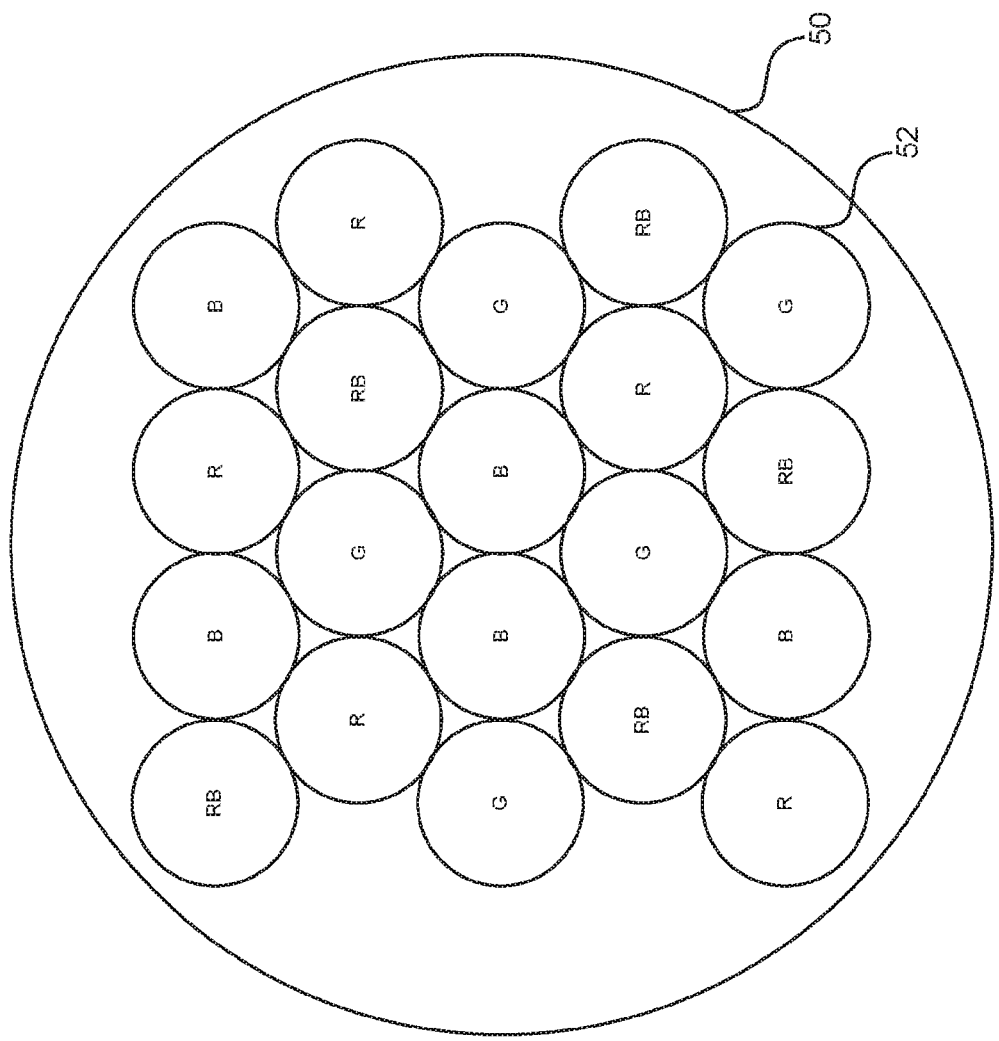
FIG. 4 shows a light source array according to an embodiment of the device.

The light source array 50 is driven to generate an excitation pulse having a duration of between 200 and 500 μs, pulsed at between 10 and 50 Hz. In an exemplary embodiment, the light source array 50 generates an excitation pulse having a duration of 400 μs pulsed at 40 Hz. The excitation pulse generated by the embodiment shown in FIG. 4 is a composite pulse of light having multiple wavelengths. The multiple wavelength excitation is achieved with an array of LEDs 52 of different colours, covering the spectral range between 400 and 640 nm. The drive current for each LED 52 is chosen using the light source driver to ensure that single turnover saturation is achieved within the duration of the excitation pulse. An LED rail voltage of +22V is required to drive the LEDs 52.

In some embodiments, the light source array 50 is an array of twenty LEDs 52, arranged in four banks of five connected in series. As shown in FIG. 4, the light source array 20 generates light using Royal Blue, Blue, Green, and Red LEDs. Respectively, the different LEDS 52 preferably emit light having central wavelengths of about 450 nm, 470 nm, 530 nm, and 624 nm, although the skilled person would recognise that Royal Blue light has a wavelength of about 450 nm, Blue light has a wavelength of about 470 nm, Red light has a wavelength of between 620 nm and 720 nm, and Green light has a wavelength of between 495 nm and 570 nm. Different groups of phytoplankton react more strongly to different wavelengths of radiation. In other words, by using multiple wavelengths, the cell counting device 2 is able to count cells from a wide range of species. By exciting all major pigment groups found in phytoplankton, it can be determined to a high probability that a negative result is a true indicator that the number of living algae present in the sample is less than a threshold.

In alternative embodiments, the Green and Red LEDs can be replaced with Royal Blue and Blue LEDs. This provides the advantage of an increase in the intensity of the illumination at Royal Blue and Blue frequencies, which decreases the response time of the phytoplankton. In further embodiments, the LEDs 52 in the array all emit the same colour of light to further increase the intensity of illumination at a particular wavelength.

In alternative embodiments, the light source array 50 comprises a plurality of lasers, each emitting light at a different spectral wavelength. The plurality of lasers are configured to emit light covering the spectral range between 400 and 640 nm. In an exemplary embodiment, the plurality of lasers emit light at 450 nm, 470 nm, 530 nm and 634 nm respectively. In further embodiments, the light source array 50 comprises a single laser configurable to emit light at a plurality wavelengths. In an exemplary embodiment, the single laser is configurable to emit light at 450 nm, 470 nm, 530 nm, and 634 nm.

The light source array 50 is configured to generate a photon flux density of 20,000 micromoles of photons per metre squared per second, which is several times the photon flux density of sunlight, within the wavelength range.

Where the cell counting device 2 is integrated into a closed system, or, in other words, is integrated into the ballast tank of a vessel, the processor 20 may be configured to prevent ballast water being emptied when the detected number of live phytoplankton is greater than a predetermined limit. Alternatively, or additionally, the processor 20 may be configured to activate a means for killing the live phytoplankton, which can include treatment processes such as: de-oxygenation, filtration, ultraviolet radiation, ozonation, and various chemical treatments, including electro-catalytic chlorination, peracetic acid, hydrogen peroxide, perchloric acid, and chlorine dioxide. This prevents the ballast water, containing more than a threshold density of live phytoplankton cells from being output into the sea. By integrating the cell counting device 2 into a closed system, the vessel is able to store fewer chemicals, and expend less energy, as the ballast water is only treated when the cell counting device 2 determines it is necessary to do so.

An external pump is used to deliver the sample 1 to the chamber 70. For example, a pump in the closed system described above may pump the sample 1 into the chamber 70. In other embodiments, the cell counting device 2 further comprises a pump for delivering the water sample 1 to the chamber 70.

The proprietary software running on the connected computing device analyses the data provided by the cell counting device 2 in near-real time. The system can be configured to analyse individual discrete samples or a continuous stream of discrete samples. The latter application uses a stop-flow system.

Figure 5:
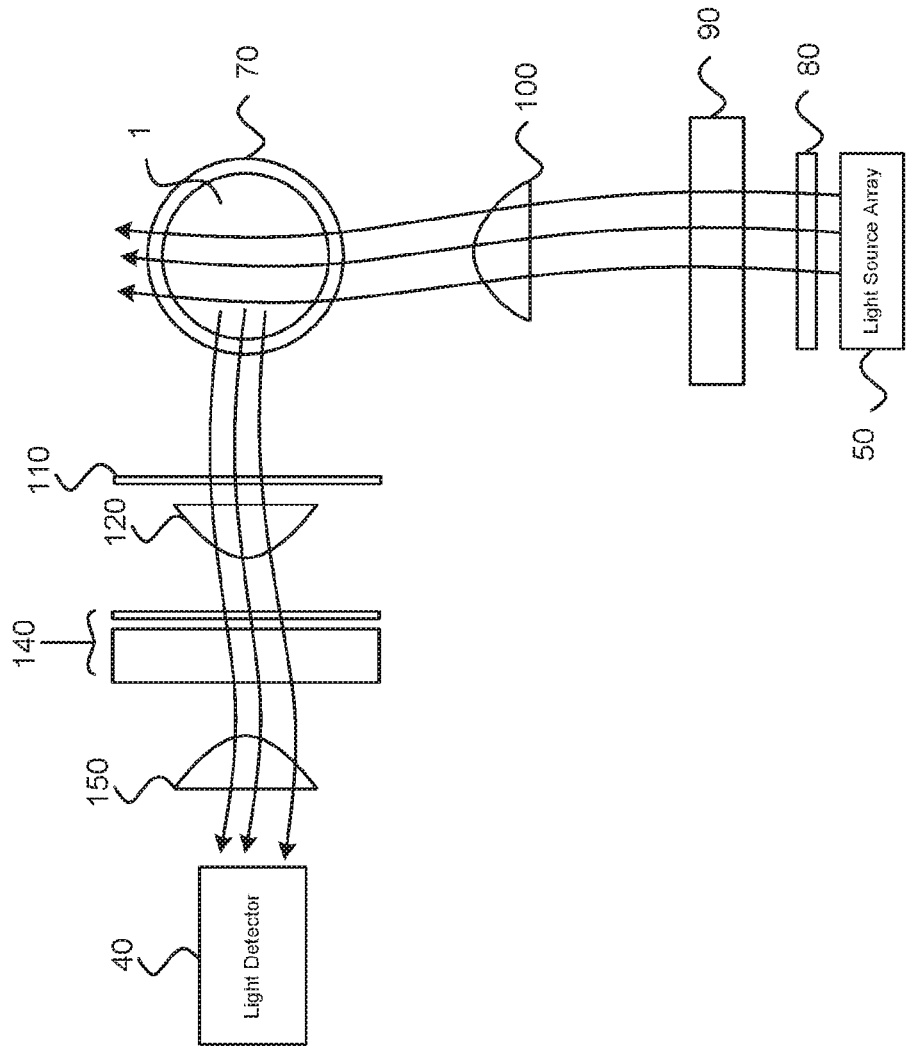
FIG. 5 shows an optical arrangement of the cell counting device shown in FIG. 3.

An optical arrangement for measuring the fluorescence of a sample 1 is shown in FIG. 5. The fluorometer is arranged with a right-angled excitation/emission geometry.

The optical design of the cell counting device 2 is optimised to direct the greatest amount of the light output from the light source array 50 into a chamber 70. The chamber 70 is made of any suitable non-luminescent material. The chamber 70 may be made of fused-silica, for example. Alternatively, the chamber 70 may be made of Pyrex, acrylic, or glass. The chamber 70 for holding the sample 1 is part of the cell counting device 2, despite not being shown in the system diagram of FIG. 3. The chamber 70 is open-ended, to allow continuous flow-through of the sample 1 when the valve 215 is opened.

To achieve this optimisation, an array of plano-convex lenses 80 is positioned directly in front of the light source array 50 to roughly collimate the output from each light source 52 in the light source array 50. A shortpass interference filter 90 is placed in front of the array of plano-convex lenses to block any longer wavelength emission from the light sources 52 that could be picked-up at the fluorescence detection wavelengths. In other embodiments, a shortpass filter, such as a shortpass coloured glass filter, is used in place of the shortpass interference filter 90. The light source array 50 is placed in the back focal plane of an achromatic doublet lens 100, which effectively produces an image of each light source 52 die at infinity. However, this also has the effect of converging the output from each light source 52 at the front focal plane of the achromatic doublet to produce a uniform distribution of light intensity. This convergence point is positioned at the centre of the sample chamber 70. The use of an achromatic doublet lens 100 ensures that the same focal point is achieved for each of the four excitation wavelengths. The uniform light distribution is further improved by using the LED colour distribution shown in FIG. 4.

The combination of the light source array 50 and array of plano-convex lenses 80 provides homogeneous illumination to an interrogated volume of between 1% and 5% of the total volume of sample 1 within the sample chamber 70. In an exemplary embodiment, the interrogated volume is 0.5 mL within a 20 mL sample 1 volume. That is to say, in an exemplary embodiment, the interrogated volume represents 2.5% of the sample 1 volume.

Figure 6:
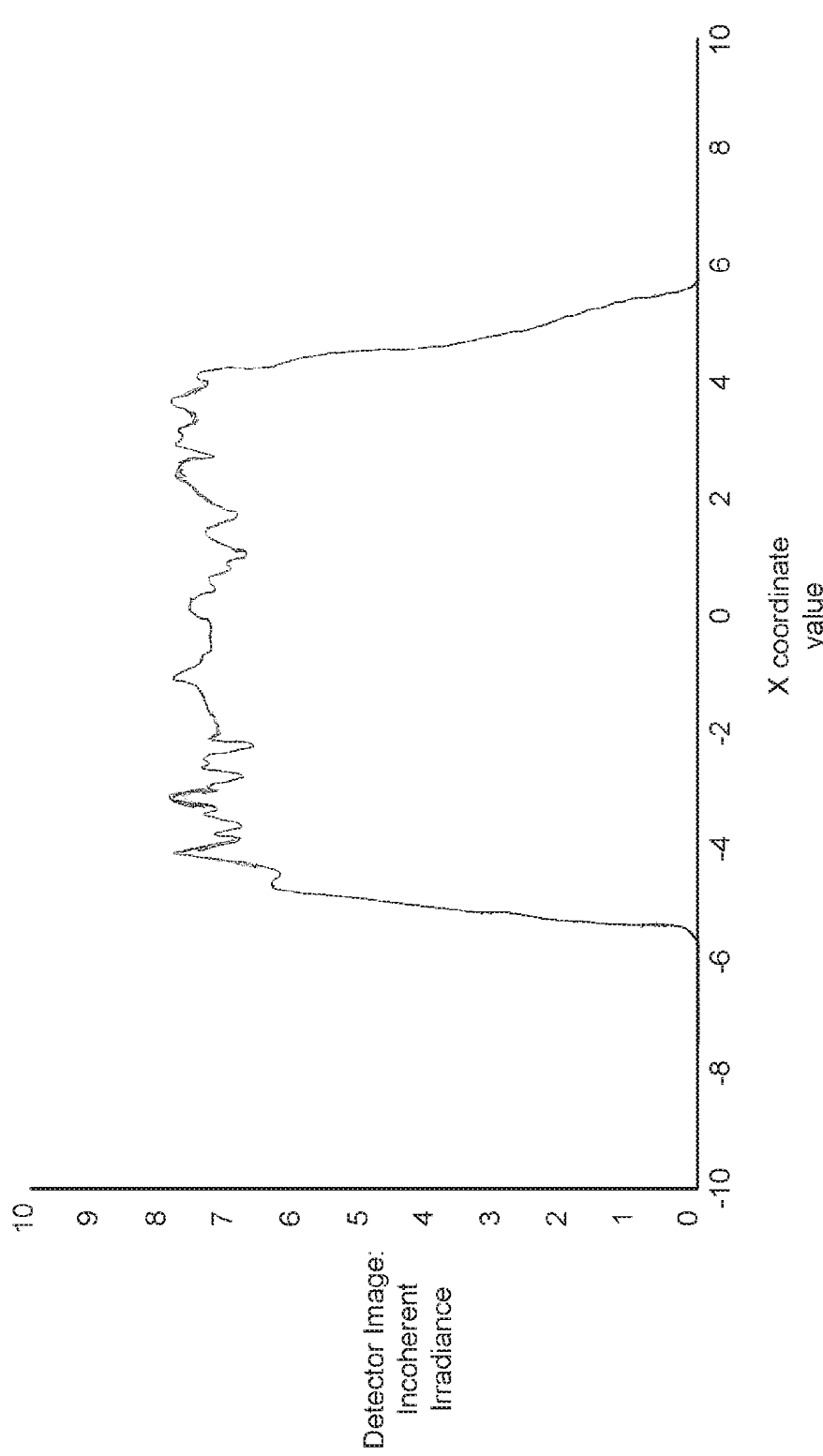
FIG. 6 shows a cross section of an illumination field generated by the optical arrangement shown in FIG. 5.

The uniform distribution of light is shown in FIG. 6. The graph in this Figure shows light intensity plotted against position. In other words, the Figure shows light intensity being roughly the same across the width of the chamber 70. A uniform light field directed into the chamber 70 provides the advantage of reducing the number of artefacts in the measurement response. If all live phytoplankton within the sample 1, particularly within the interrogated volume, are not subjected to the same light field, then they will saturate over different timescales and the signal response will be distorted. The detection optics are designed to image the central uniform illumination area onto the light detector 40. This emission path will now be described in more detail by referring back to FIG. 5.

The emission path is a condenser arrangement for collimating the fluorescence emitted from the interrogated volume. The emission path comprises a first plano-convex lens 120 and a second plano-convex lens 150 sandwiching an optical filter 140. The optical filter 140 may be chosen to remove wavelengths of light from the collimated light that are not within the spectral range of fluorescence emitted by PSII within live phytoplankton cells. For example, the optical filter 140 is a bandpass interference filter with a peak at 682 nm and a half band width of 30 nm. However, the optical filter 140 may also be a suitable longpass interference filter, longpass absorptive filter or dichroic filter. Preferably, the optical filter 140 is arranged to transmit chlorophyll fluorescence at 683 nm. The focal length of these lenses is selected to ensure that the area of uniform illumination generated across the interrogated volume is imaged onto the active area of the light detector 40.

Apertures (not shown) are arranged throughout the emission and excitation optical paths to minimise interference from scattered light.

FIG. 7 shows a perspective view of the cell counting device 2 according to an embodiment. The cell counting device 2 comprises an outer case 220. The outer case 220 includes a hinge 180 for coupling the outer case 220 to a lid (not shown). The outer case 220 further comprises data ports 170 (or interfaces) for connecting the cell counting device 2 to another device, such as a computing device, by wired connection such as by USB and/or Ethernet cable. In some embodiments, wireless communication between the cell counting device 2 and a computing device is also possible through Bluetooth communication or any other known wireless communication means. The case 220 further comprises a charger socket for connecting the water ballast monitoring device 2 to an external power supply, such as the electricity supply of a ship. Waterproof bulkhead connectors are used for these connections.

The skilled person would appreciate that many of the processing steps described herein could be carried out on the external computing device. A system comprising the cell counting device 2 and the external computing device could be used to achieve the advantages described herein, where the cell counting device 2 transmits information associated with the received light to the external computing device so that the external computing device can perform the processing steps to estimate cell density.

The cell counting device 2 weighs less than 4 kg. The size of the cell counting device 2 (excluding connectors) does not exceed 340×220×100 mm.

The cell counting device 2 comprises a top plate 160, which incorporates the display 60 and external electrical connections 170. An optics block is mounted underneath the top plate 160 to support the chamber 70, associated optics and fluid paths and the main electronics boards, namely: the processor 20, light detector 40 and light source array 50 driver boards. The power supply 10 is mounted separately to the top plate 160. A metal enclosure (not shown) provides EMC screening for the fluorometer.

External fluid connectors 210a, 210b are located at the side of the case 220. The external fluid connectors 210a, 210b are in fluidic communication with the inside of the chamber 70. This will be shown in more detail in FIGS. 8a and 8b. The two fluid connectors 210a, 210b are ⅜"BSP ports that provide standard threaded connectors. In some embodiments, ½"BSP connections are used. The external fluid connectors 210a, 210b may be coupled directly to the pipework within the vessel's ballast water treatment system.

The cell counting device 2 is configurable to operate in both discrete-sampling mode and stop-flow mode. In some embodiments, switching between these two modes is achieved by swapping blocking members 190, 195. Here, the blocking members 190, 195 are threaded inserts, but in other embodiments the blocking members 190, 195 may be retained by friction or a clip, rather than a screw thread. In the example shown in FIG. 7, the cell counting device 2 is configured to operate in discrete-sample mode. The blocking member 195 inserted approximately opposite the fluid connectors 210a, 210b determines the mode of operation. The other blocking member 190 is in a stored position, and does not perform a function until moved to the position approximately opposite the fluid connectors 210a, 210b.

In some embodiments, such as those capable of operating in stop-flow mode, taps or valves attached to either or both the upper fluid connector 210a or lower fluid connector 210b act as blocking members to allow a sample 1 to enter or leave the chamber 70. No tools are required for routine operations, including switching between stop-flow and discrete-sample modes. Other embodiments operate in discrete sampling mode, only.

Discrete-sample and stop-flow modes will now be described in more detail with reference to FIGS. 8a and 8b, which show different embodiments of the cell counting device 2. In discrete-sample mode (FIG. 8a), a blocking member 195 in the form of a solid funnel insert is provided to block the upper fluid connector 210a and prevent ambient light from outside the device 2 affecting the measurement of fluorescence after the sample 1 has been poured into the chamber 70 through the top plate 160. The upper portion of the walls of the chamber 70 are chamfered to receive the funnel insert, and the upper fluid connector 210a penetrates the upper portion of one of the walls of the chamber 70.

The sample 1 drains through the lower fluid connector 210b, which is fitted with a tap (or valve) 215 to control liquid flow, after the measurement has been taken. Alternatively or additionally, the lower fluid connector 210b is fitted with a light-tight cap 216 which functions to block the flow of sample 1 when the tap 215 is not fitted. A separate light tight cap 216 may optionally be provided at the upper fluid connector 210a to further eliminate interference from ambient light.

Figure 8B:
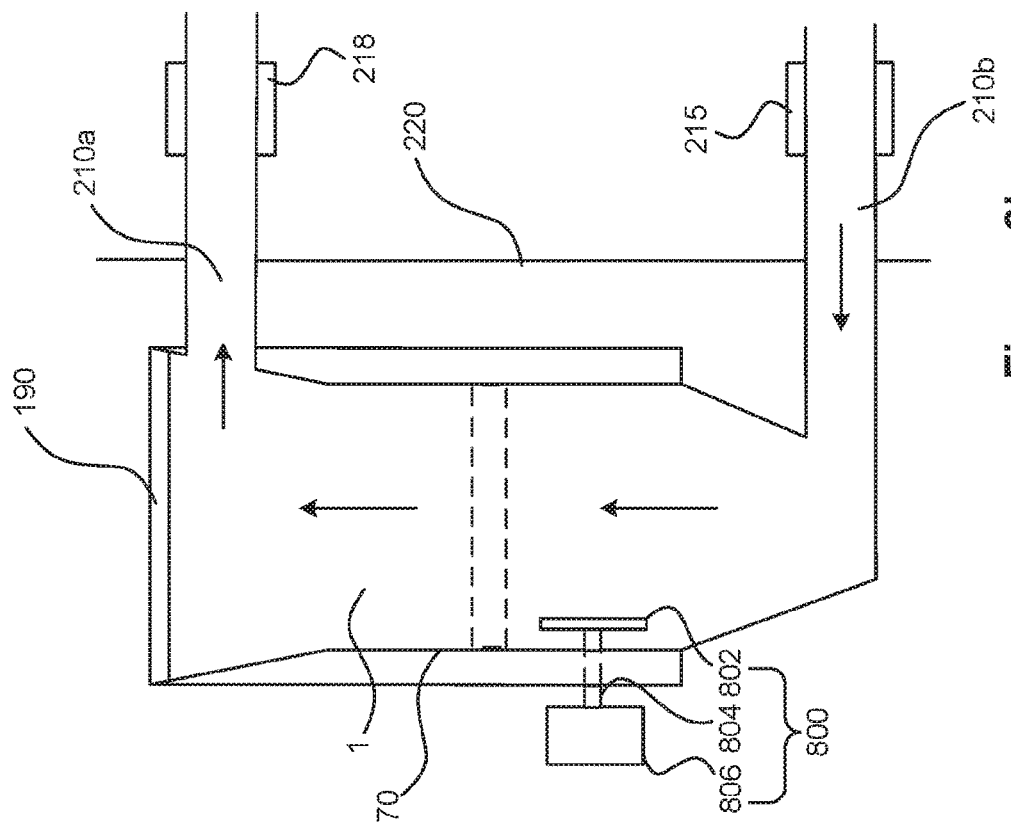
FIGS. 8a and 8b show cross sections of embodiments of the cell counting device of FIG. 7, operating in discrete-sampling mode and flow-through mode respectively.
Figure 8A:
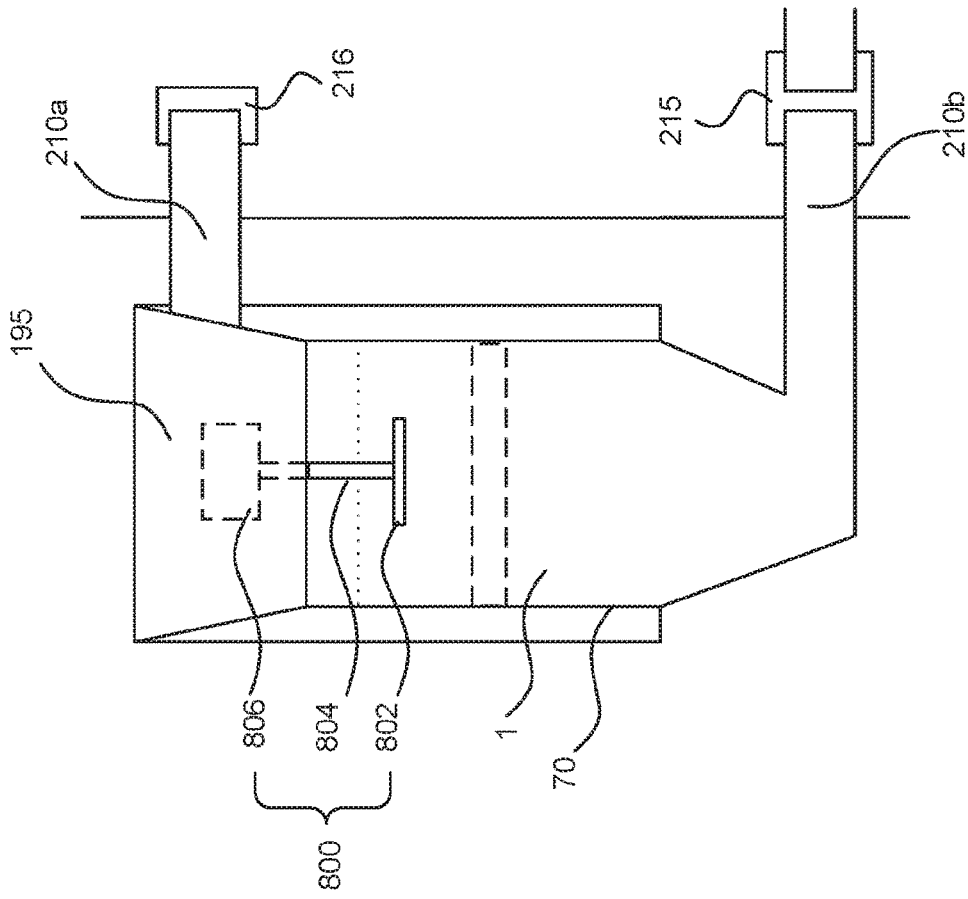

The region of the sample 1 interrogated by the fluorometer is represented by the dashed rectangle in FIG. 8a. The sample within this region is called the interrogated volume (or, in other words, the sub-sample).

A stirrer 800 is integrated with the blocking member 195. One end of the stirrer 800 is an elongate horizontal member 802 arranged to extend into the sample 1 when the sample 1 is in the chamber 70, but not into the interrogated volume. The stirrer 800 also includes a shaft 804 for coupling the elongate horizontal member 802 to a motor 806.

The motor 806 rotates the shaft at a frequency of between about 1 Hz and about 20 Hz. Typically, the stirrer 800 operates at 2 Hz. To control the frequency of rotation, the motor 806 may include a gearbox. For example, the gearbox may be a 60:1 gearbox. The motor 806 may be powered by an external power supply, or may be electrically coupled to the power supply 10 of the cell counting device 2.

The blocking member 195 having the integrated stirrer 800 may have electrical contacts that electrically couple to corresponding electrical contacts arranged around the mouth of the chamber 70. Therefore, when the blocking member 195 is inserted into the chamber 70, the motor 806 is supplied with power from the power supply 10. The motor 806 may be automatically activated, or may be activated by means of a manual switch.

Alternatively to an elongate horizontal member 802, the shaft 804 of the stirrer 800 may be coupled to a flat plate, a blade, paddle, or a whisk. In other words, the stirrer 800 may comprise any suitable means for mixing the sample 1 so that the water within the interrogated volume opposite the light detector 40 is exchanged with the rest of the sample 1.

To enter stop-flow mode, the blocking member 195 is replaced by a blocking member 190 in the form of a light-tight cap that does not block the upper fluid connector 210a. Here, the light-tight cap may incorporate a stirrer 800 as previously described. Alternatively, the blocking member 195 may be replaced by a blocking member 190 in the form of a funnel having a fluid flow path therein for allowing water to enter the upper fluid connector 210a from the chamber 70. Here, the stirrer 800 passes through the side of the chamber 70. In the stop-flow mode, the tap 215 on the lower connector fluid connector 210b is used to control the cell counting device 2 to continuously allow discrete samples 1 to enter and leave the chamber 70.

Another embodiment of the cell counting device 2 will now be described with reference to FIG. 8b, which shows the cell counting device 2 operating in stop-flow mode in more detail. Here, the stirrer 800 is integrated with the side wall of the chamber 70, but the blocking member 190 may incorporate the stirrer 800 instead. Taps (or valves) 215, 218 fixed to the upper and lower fluid connectors 210a, 210b act as blocking members that can be opened or closed to allow or prevent the sample 1 from leaving the chamber 70. In other words, the taps 215, 218 cause the cell counting device 2 to stop freely flowing water and enter discrete-sample mode while the same blocking member 190 in the form of a light-tight cap is installed. Controlling the valves 215, 218 stops or allows the flow of water, so that a first discrete sample is released and another discrete sample can immediately enter and become stored in the chamber 70 when the measurements on the first discrete sample are complete. This stop-flow mode is particularly useful when the cell counting device 2 is integrated with a vessel.

Opening the taps 215, 218 results in a continuous flow path from the outside of the case 220, through the lower fluid connector 210b, through the chamber 70 and out of the case 220 through the upper fluid connector 210a. The blocking member 190 prevents ambient light from entering the chamber 70. It would be readily understood that the flow of ballast water can be reversed, so that the sample 1 enters the chamber 70 via the upper fluid connector 210a.

The blocking member 190 is a light-tight cap that is screwed onto the mouth of the chamber 70. Alternatively, the blocking member 190 may also be secured by friction or clamps. Alternatively, the blocking member 190 may be fixed and essentially forms a wall of the chamber 70.

Installing the stirrer 800 in the side of the chamber 70 is effective in stop-flow mode as it allows the sample 1 to flow into or out of the chamber 70 with reduced obstruction.

Alternatively to the embodiments shown in FIGS. 8a and 8b, in some embodiments the upper fluid connector 210a does not penetrate the wall of the chamber 70. Instead, the blocking member 190 has a fluid flow path therein for fluidly coupling the chamber 70 to the upper fluid connector 210a in stop-flow mode. Here, instead of a cap or a funnel, the blocking member 190 is a rectangular housing. The blocking member 195 for discrete-sample mode, having the stirrer 800 installed therein, does not have a fluid flow path, and so presents a barrier between the chamber 70 and the upper fluid connector 210a. The upper surface of the blocking members 190, 195 prevents light from entering the chamber 70.

In other embodiments where the upper fluid connector 210a does not penetrate the wall of the chamber 70, the blocking member 190 is in the form of a hollow funnel through which a sample 1 can be poured. A separate light-tight cap, similar to the blocking member 190 shown in FIG. 8b, is provided for covering the blocking member when a measurement is being taken. The tap(s) 215, 218 prevent the sample 1 from leaving the chamber 70.

In embodiments not having valves 215, 218 arranged on the upper or lower fluid connectors 210a, 210b, a light-tight (opaque) cap 216 is provided at least on the lower fluid connector 210b for allowing a sample 1 to leave the chamber 70 after a measurement in discrete-sample mode has been performed.

FIGS. 8a and 8b are not drawn to scale in order to improve clarity. In reality, the flow path between the bottom of the chamber 70 and the tap 215 is relatively small compared to the volume of the chamber 70. The chamber 70 typically holds a sample size of 20 mL. The interrogated volume is typically 0.5 mL. In other words, the interrogated volume is typically about 2.5% of the sample volume, and so the volume of any one sub-sample is 2.5% of the volume of the sample 1.

Figure 10:
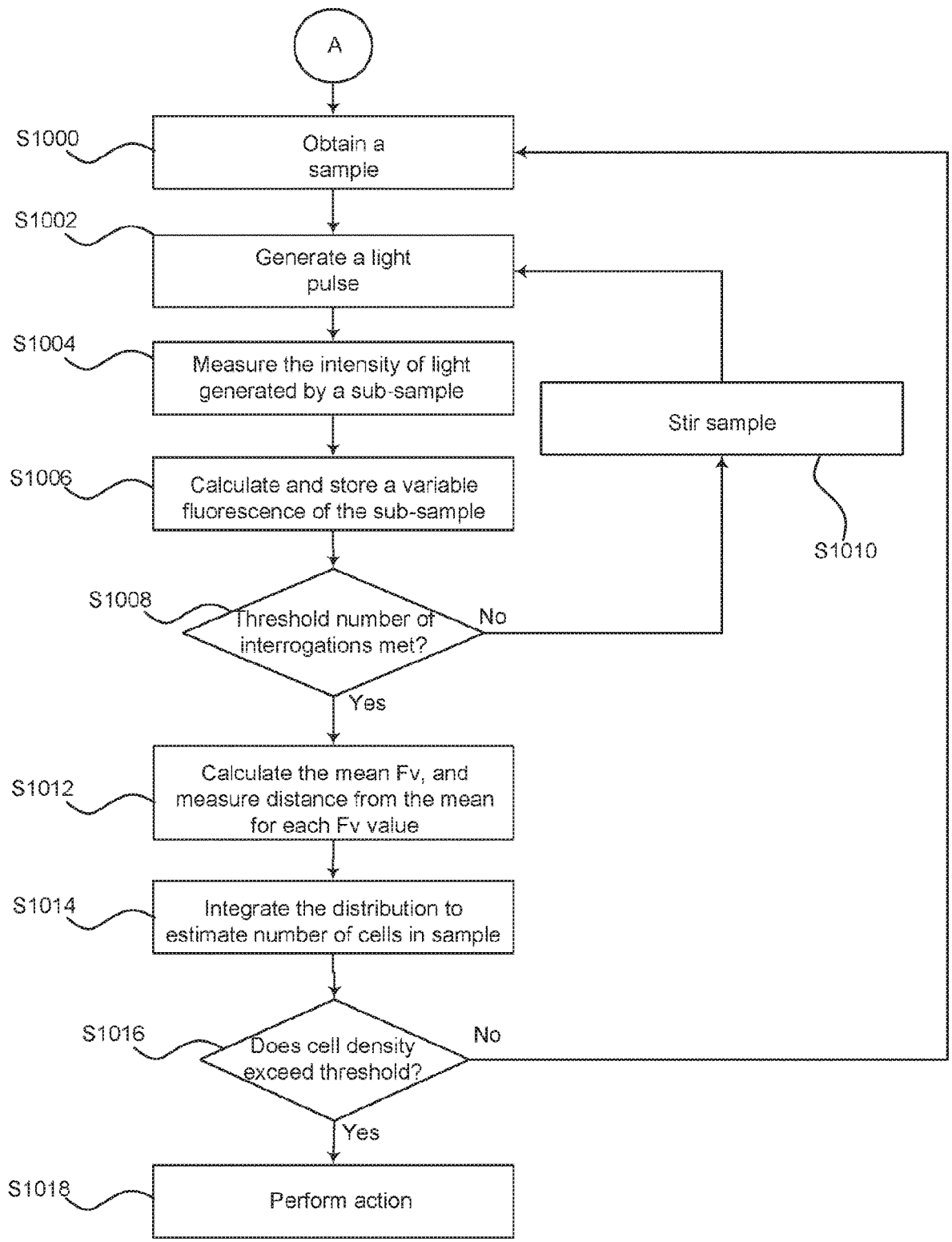
FIG. 10 is a flowchart of a cell counting process according to an embodiment of the present invention.

It would be readily understood that the methods described herein, particularly with reference to FIG. 10, can be applied to any well-mixed body of water, providing the interrogated volume represents a small proportion of the total. For example, a well-mixed cubic metre of water could be interrogated using a stop-flow system.

Figure 9:
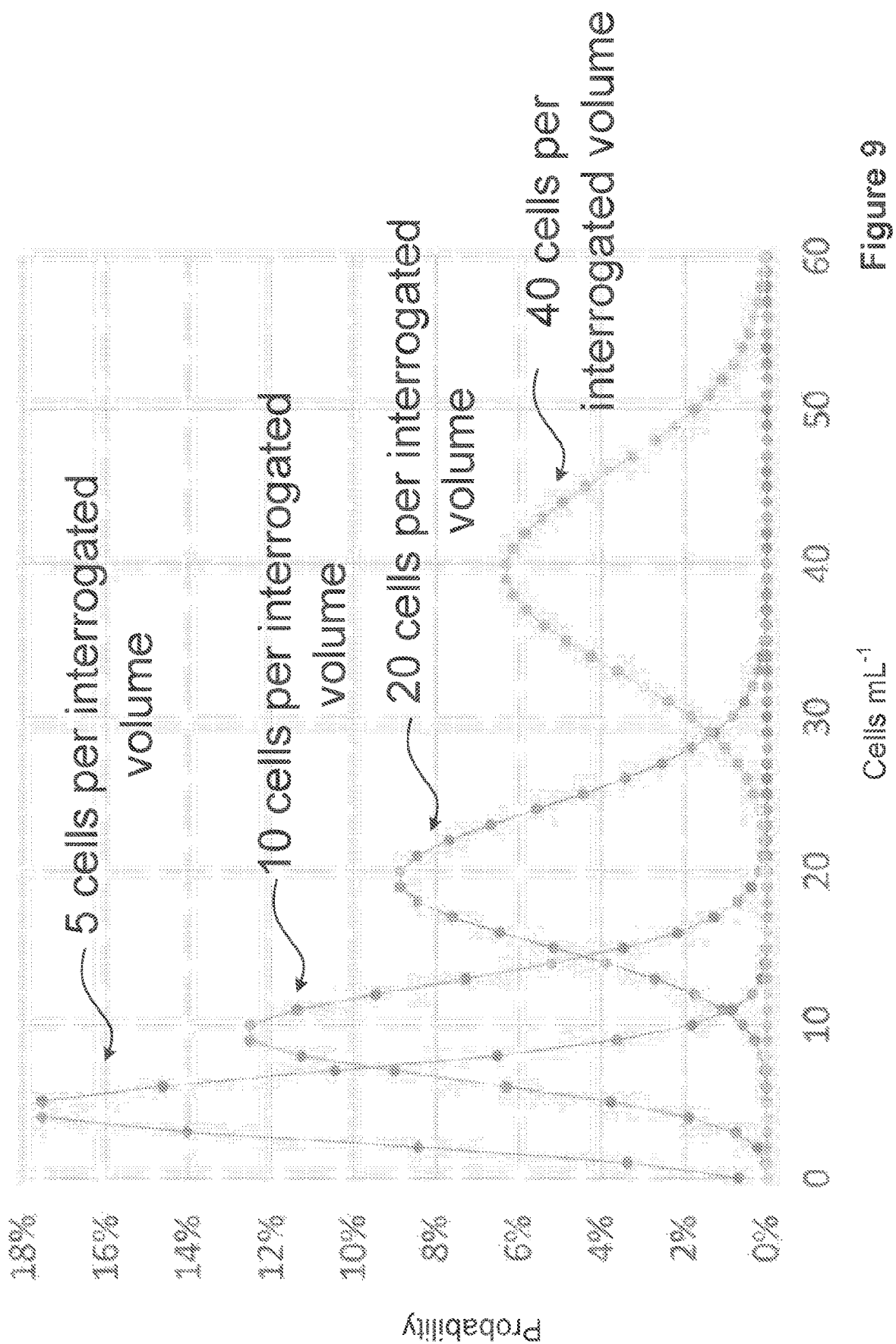
FIG. 9 shows a Poisson distribution of cells per millilitre of sample.

FIG. 9 shows the expected Poisson distribution of cell counts in 0.5 mL interrogated volumes (or, in other words, sub-samples) within a larger sample of ballast water containing 5, 10, 20 or 40 cells per integrated volume (which is 0.5 mL in the example). The Poisson distribution is a plot of cell density against probability. The graph shows that for a small interrogated volume within a larger sample of a known average cell density, the chance of finding that same cell density in the interrogated volume is high. However, where the average cell density is high, for example greater than 10 cells per mL, the chance of the cell density of the interrogated volume being a density other than the average becomes greater than it would be at lower densities. In the context of ballast water analysis, the most important feature of these distributions is that the spread of values, relative to the mean value, becomes narrower with increasing cell density.

The very high signal to noise ratio (SNR) provided by the cell counting device 2 described with reference to the previous Figures allows for an accurate determination of $F_v$ from a discrete sample in less than ten seconds. However, as shown in Table 1 below, the large range of $F_v$ per cell values within the 10 µm to 50 µm range severely limits the translation of $F_v$ to cell density. In addition, the Poisson distribution within the sample can introduce a very significant error at low cell density, as shown in FIG. 9.

More specifically, at step 1002, a pulse of light is generated and directed towards the interrogated volume. The pulse of light, according to some embodiments, is generated using a plurality of light sources 52 and comprises light having a plurality of wavelengths. The pulse of light has a duration of between 200 and 500 µs, and is pulsed at between 10 and 50 Hz. In an exemplary embodiment, the pulse of light has a duration of 400 µs and is pulsed at 40 Hz to saturate PSII. The pulse of light is projected onto the interrogated volume using lenses so that a uniform light field is spread across the interrogated volume. For example, one of the lenses is an achromatic doublet lens 100 to direct light of multiple wavelengths into the chamber 70 such that the interrogated volume is illuminated with a uniform light field. In other embodiments, the plurality of light sources 52, producing light of different wavelengths, are located on a curved surface such that the interrogated volume is illuminated with a uniform light field.

Preferably, the interrogated volume is 2.5% of the volume of the sample 1. For example, when the sample 1 is 20 mL, the sub-sample is 0.5 mL.

At step 1004, the time-dependent response of the interrogated volume is measured. In other words, the intensity of the light generated by the interrogated volume in response to being illuminated by the pulse of light is measured. The response is measured at time intervals much less than the duration of the pulse of light. For example, the intensity is measured at 1 µs intervals, before, during and after the pulse

TABLE 1

Cell species information

| Species | Shape | Smallest dimension (µm) | Volume (µm$^3$) | $F_v$ cell$^{-1}$ | PSII complexes cell$^{-1}$ |
|---|---|---|---|---|---|
| Emiliania huxleyi | Spherical | 5-10 | 65-525 | 0.00022 | 9.3 × 10$^5$ |
| Phaeodactylum tricornium | Fusiform - Triradiate and Ovoid | 2-4 | 160-530 | 0.00019 | 1.25 × 10$^6$ |
| Dunaliella tertiolecta | Ovoid | 6-10 | 200-1000 | 0.00022 | 1 × 10$^6$ |
| Dunaliella salina | Spherical | 10-12 | 525-905 | 0.00018 | 6.5 × 10$^5$ |
| Thalassiosira weissflogii | Cylindrical | 5-16 | 880-28000 | 0.00073 | 2.1 × 10$^6$ |
| Thalassiosira punctigera | Cylindrical | 30-60 | 63500-430000 | 0.01702 | 5.6 × 10$^7$ |

FIG. 10 shows a method of estimating cell density (or concentration) using the cell counting device 2 previously described, according to an embodiment of the present invention. The method is implemented on the processor 20. This method is labelled Process A.

In a first step S1000, a sample 1 is obtained. A sample 1 is, for example, ballast water in the hull of a waterborne vessel. The sample 1 may be obtained in discrete-sample mode by a user pouring the sample 1 through the mouth of the chamber 70, or in stop-flow mode where the continuous flow of water passing through the chamber 70 is stopped using taps 215, 218 to leave a sample 1 in the chamber 70.

In steps 1002 to S1006, the variable fluorescence of an interrogated volume within the sample 1 is determined. As now described, the present invention utilises the modified FRR "single turnover" technique. However, the invention is not limited to this method, and although slower and less accurate, can also be used in conjunction with multiple turnover techniques.

of light is emitted. The intensity is measured at time intervals less than the duration of the pulse of light.

The variable fluorescence ($F_v$) of the interrogated volume is calculated at step S1006. Furthermore, the $F_v$ value for the interrogation is stored, for example in memory 25. Calculating $F_v$ involves estimating a minimal fluorescence ($F_o$) of the interrogated volume using linear regression, and subtracting that value from the maximal fluorescence ($F_m$), which is where the fluorescence of the interrogated volume peaks.

In more detail, $F_o$ is calculated as follows. Linear regression through the first 60 points (at one microsecond a point) is applied. The results from this 60 point regression (slope, intercept and standard error) are set as reference values. The number of points in the regression is then decreased, in steps of 2, down to 20 points. If the slope is higher and the standard error is lower at any step, the results from that step become the reference values. $F_o$ is calculated through extrapolation of the final reference regression line to zero time. The slope of the increase in fluorescence decreases between $F_o$ and $F_m$, even over the first few microseconds. Consequently, the shorter the regression line, the better the fit. The requirement for a lower standard error imposes a quality check. If the signal to noise is high, the reference regression line is at or close to 20 points.

To calculate $F_m$, linear regression through the last 240 points (at one microsecond a point) is applied. If the slope is positive (still increasing) or flat, $F_m$ is set by extrapolating to the end of the pulse. If the slope is negative (starting to decrease), $F_m$ is set by extrapolating to the start of the pulse. If the slope is positive, saturation has not been reached. Consequently, the extrapolation should be to the end of the pulse. A negative slope is indicative of known artefacts, which quenches $F_m$ from the maximum level. Extensive testing has shown that extrapolating to the start of the pulse minimises the error generated by this quenching.

At step S1008, it is determined whether a threshold number of interrogations (may also be referred to as cycles or iterations) has been met. For example, a data set of 240 values of $F_v$ is generated by averaging 40 sequences at 40 Hz for 4 minutes. Here, the threshold number of interrogations is 240.

If the threshold number of interrogations is not met, the sample is stirred in step S1010, and steps S1002 through S1008 are then repeated. The sample 1 is stirred using the stirrer 800. This ensures that all liquid within the sample 1 enters the interrogated volume, or the region opposite the light detector 40, at some point during the test. For example, the sample 1 is stirred at a speed that provides an optimum rate of interrogated volume exchange with the sample 1. The speed of rotation of the stirrer 800 may be between 0.1 Hz and 20 Hz. Typically, the stirrer 800 operates at 2 Hz.

Figure 11:
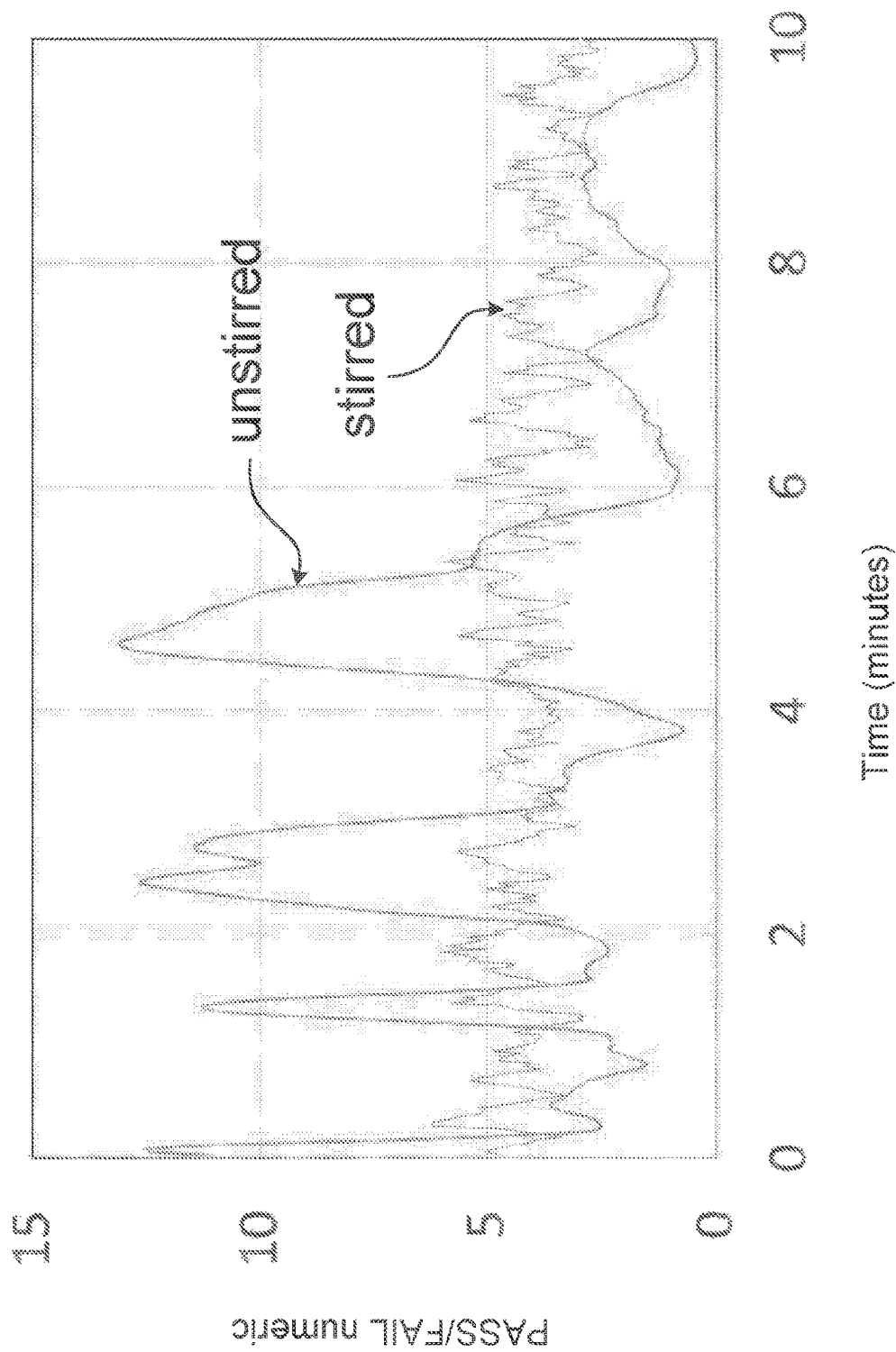
FIG. 11 is a graph showing the effect of stirring the sample.
Figure 12:
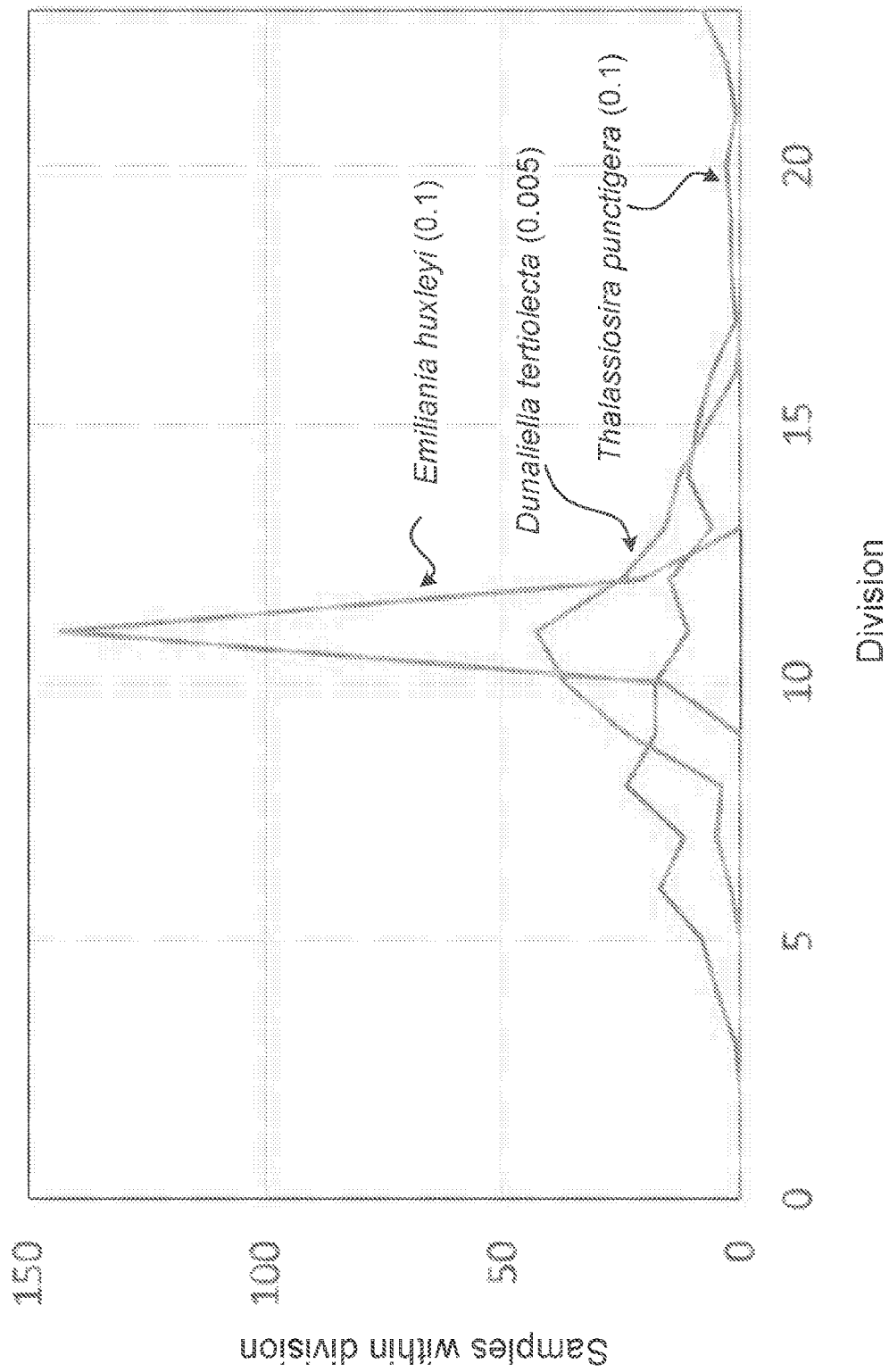
FIG. 12 is a histogram showing the distribution of variable fluorescence across a number of interrogations for three species of phytoplankton.

The effect of stirring the sample 1 is evident from FIG. 11. Here, it is clear that stirring the sample 1 reduces the variability of $F_v$ values for each interrogated volume, and consequently a more accurate representation of the sample 1 as a whole can be obtained. For example, a sharp peak in $F_v$ may occur when a colony of phytoplankton enter the interrogation region, giving the impression that the sample 1 has a high cell density. By mixing the sample 1, the colony is broken up, and the cell density across the sample 1 as a whole is made more homogeneous.

In other words, the combination of a relatively large sample 1 volume, high ratio of sample volume to interrogated volume (sub-sample) and the stirring device 800 is effective in neutralising sampling errors associated with the Poisson distribution of phytoplankton cells within ballast water discharge or other water sample, without the need to concentrate cells by centrifugation or filtration.

Figure 13:
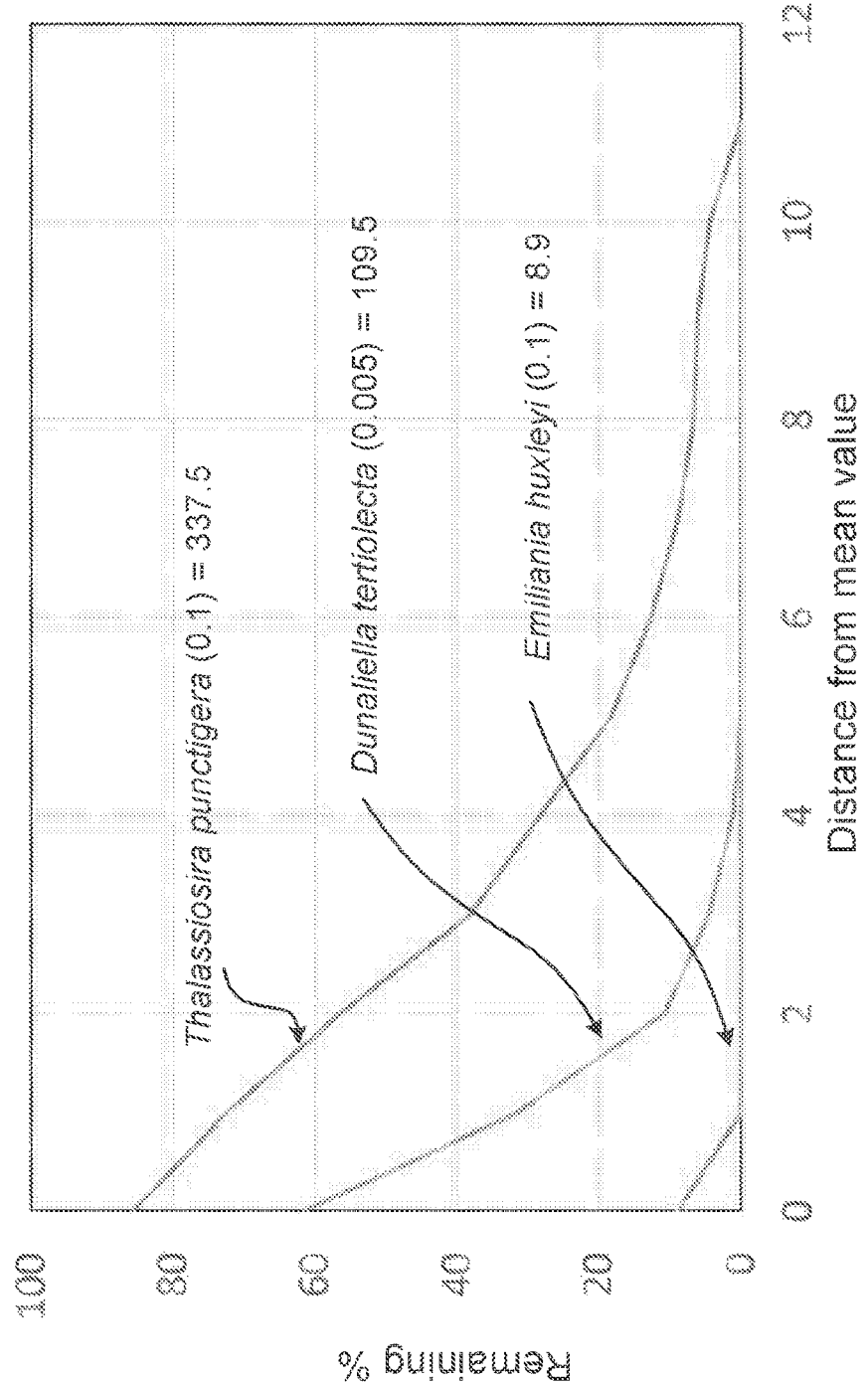
FIG. 13 is a graph showing the distance from the mean value of fluorescence for three species of phytoplankton.

If the threshold number of interrogations is met, at step S1012 the average $F_v$ value across the number of interrogations is calculated. Furthermore, the distribution of each $F_v$ value in relation to the average is also calculated. The distribution of $F_v$ values for three different species of phytoplankton is shown in FIG. 13.

The number of cells within the sample 1 is then estimated in step S1014 by integrating the distribution calculated in step S1012.

In step S1016, it is determined whether the estimated number of cells per mL (or cell density) exceeds a threshold, such as that defined in the USCG BWDS. The cell density is estimated by dividing number of cells estimated in step S1012 by the volume of the sample 1. If the estimated cell density exceeds the threshold, at step S1018 an action is performed. The action may be indicating that the sample 1 is not compliant with the IMO D2 Standard (10 μm to 50 μm) and the US Coast Guard Discharge Standard (10 μm to 50 μm), using the display 60, an indicator light or an audible alarm either on the cell counting device 2 or on an external computing device. Alternatively, the action may be controlling a means for exterminating live phytoplankton, such as a ballast water treatment system.

As the method making use of the Poisson distribution as described with reference to FIG. 10 optimally requires the sample 1 to be interrogated for 4 minutes (or in some embodiments, 6 to 8 minutes), it is not appropriate to perform the method on a continuous flow of water. That being said, vessels such as oil tankers can have ballast tanks of large volumes, being up to 400 metres long and 60 metres in beam. It is more efficient to test the water in these vessels using a system whereby water can continuously flow through the cell counting device 2 except when measurements are being taken, as the populations of cells can vary wildly throughout the vessel.

Therefore, it is necessary to perform a stop-flow mode, where the cell counting device 2 takes an automated series of discrete-sample measurements.

Alternatively, the cell counting device 2 may operate in a continuous-flow mode first, where water is able to freely pass into and out of the chamber 70, while a coarse measurement is taken, and then the cell counting device 2 can be switched to operate in discrete-sample mode or stop-flow mode to allow a more accurate measurement to be taken. In more detail, the variable fluorescence of the sample 1 is measured, preferably using the single turnover method of the background art, where the cells are assumed to have the same variable fluorescence regardless of their size ($F_v$ per cell is fixed). When a spike in absolute $F_v$ is detected, or if the absolute $F_v$ is extremely low, the valves (taps) 215, 218 are controlled to cause the cell counting device 2 to enter discrete-sample mode. Here, a sample 1 is trapped in the chamber 70, and the steps of Process A are performed on the trapped sample 1 for 4 minutes. In some embodiments, the steps of Process A are performed for 6 to 8 minutes. In other words, the cell counting device 2 switches from continuous-flow mode to discrete-sample mode if the absolute $F_v$ of a sample 1 falls within a range of very low to very high. A very low $F_v$ is defined as being too low for a fail of the BWDSs even if $F_v$ per cell is assumed to be very low, and a very high $F_v$ is defined as being too high for a pass of the BWDSs even if $F_v$ per cell is assumed to be very high. These extremes cover a range of 3 to 4 orders of magnitude. Therefore, in most cases, the cell counting device 2 will switch to operate in discrete-sample mode or stop-flow mode.

In further embodiments, if the variable fluorescence calculated in continuous-flow mode, using the assumed $F_v$ per cell, is within the two threshold boundaries, the cell counting device 2 is configured to operate in stop-flow mode.

In stop-flow mode, the cell counting device 2 switches to discrete-sample mode at regular intervals. The action to be performed at step 1018 may be to control the cell counting device 2 to take discrete samples at more regular intervals, for example if the estimated cell density exceeds a cell density threshold, in order to perform a more detailed analysis of the sample 1 in that particular area of the ballast tank of the vessel.

In other words, when operating in stop-flow mode, there may be two thresholds of cell density. If the first threshold is exceeded, but the second threshold is not, then the cell counting device 2 increases the frequency at which discrete samples are taken (thus reducing the volume of water passing through the cell counting device 2 between measurements). If the second threshold is exceeded then an action is performed as described earlier with reference to step S1018.

Figure 14:
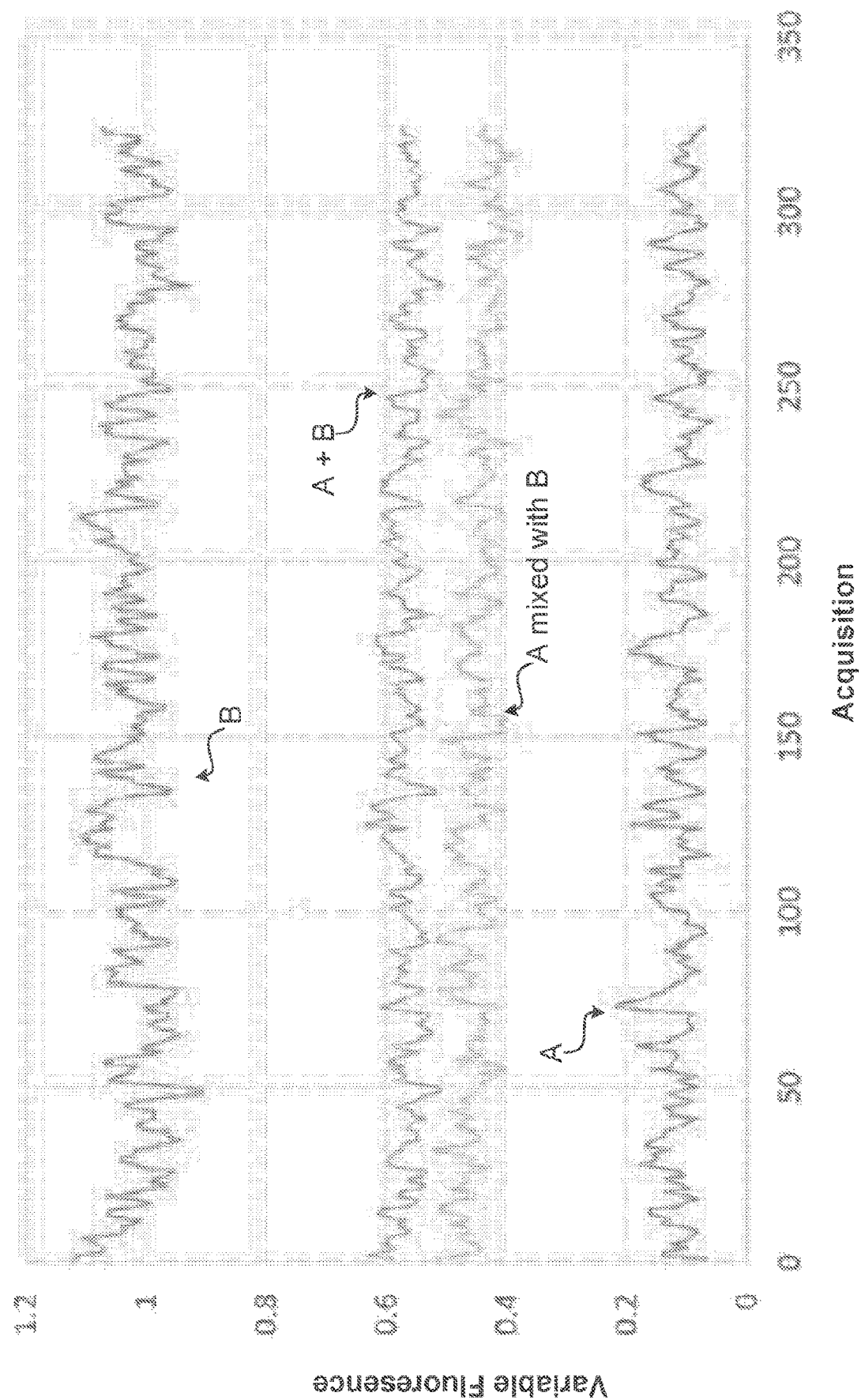
FIG. 14 is a graph showing the effect of mixing different species of phytoplankton in the same sample.

FIG. 14 shows the effect on variable fluorescence of mixing two species of phytoplankton in the same sample. The invention further provides an algorithm for estimating the concentration of cells within the sample 1 when there are a number of species of phytoplankton present. Regarding FIG. 14, Trace A represents *Thalassiosira punctigera* at a cell density of 15 per mL; Trace B represents *Thalassiosira weissflogii* at a cell density of 365 per mL; Trace C is Trace A and Trace B added together; and Trace D represents a 50:50 mix of the cells from Trace A and Trace B.

The algorithm performs the following steps. Firstly, steps S1000 to S1014 of Process A are performed in order to calculate and analyse the distribution of $F_v$ values for the sample 1. This analysis of the distribution generates an estimated cell density for the cells that contribute to the distribution (i.e. the cells that have a relatively high $F_v$ per cell value). An average $F_v$ per cell for the cells contributing to the distribution is then calculated by using the estimated cell density to calculate an estimate of the number of cells in the sample as a whole and dividing the total $F_v$ by this value.

The algorithm then estimates the proportion of the total $F_v$ signal that can be attributed to the cells that contribute to the distribution. The remaining $F_v$ is then attributed to cells that have an $F_v$ per cell value that is too small to contribute to the distribution. In an exemplary embodiment, it is assumed that the $F_v$ per cell for these smaller cells is 5% of the average for the cells that do contribute to the distribution. This is a conservative value, which minimises the chance of a false positive being generated.

For the example shown in FIG. 14, the expectation is that analysis of Trace D will give a cell density of 190 per mL, calculated at (15+365)/2. By using the algorithm as described above, cell density of Trace D was estimated to be 199 per mL, which is an error of less than 5%.

Advantages of the cell counting device 2 reside in the provision of the processor 20 for applying a modified FRR algorithm to determine the presence of phytoplankton, and to measure the concentration of the phytoplankton within a sample. This improves the accuracy of ballast water monitoring devices, so that there is a reduced chance of generating false positive or false negative results.

Figure 15:
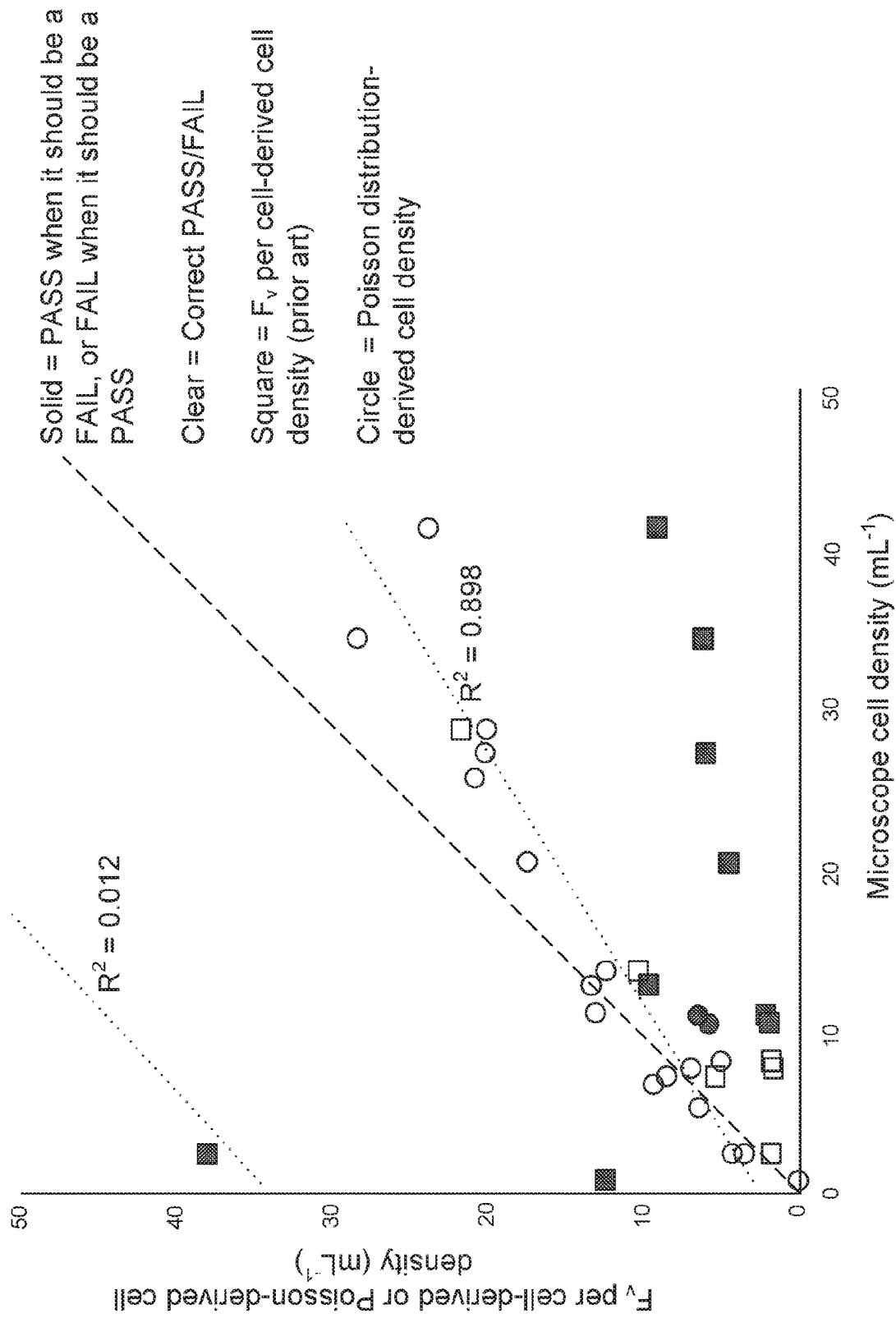
FIG. 15 is a graph showing the effect of the method according to the present invention against the effect of the prior art method.

These advantages are readily apparent from FIG. 15. FIG. 15 shows a plot of cell density within a sample as measured by a microscope, against cell density estimated using Process A (or the cell density derived by means of using the Poisson distribution according to the present invention) and cell density estimated using an estimated $F_v$ per cell regardless of cell size.

The solid circles and squares indicate estimated cell densities that are outside of the threshold set by the BWDSs, but in reality should have passed the test (or be within the threshold) according to microscope measurements. Squares represent $F_v$-derived estimates, and circles indicate estimates derived using the present invention. The large number of solid squares in relation to clear squares, and small number of solid circles in relation to clear circles, indicates that the method according to the present invention provides much more accurate estimates than prior art methods.

The cell counting device 2 has a wide range of applications beyond testing cell density of phytoplankton in ballast water discharge. The cell counting device 2 can be used to estimate the cell density within a sample of any photoactive cells, such as those in waterways or cell assays. It should also be apparent that the cell counting device 2 could be applied to any cell in suspension that exhibits a time-dependent fluorescence, for example a fluorescent probe such as a biological fluorophore or a cell laced with a photoactive organic dye.

The aforementioned embodiments generate high quality data points at high frequency (1 Hz) through the combination of very short (400 μs) measurement pulses applied at high frequency (40 Hz) plus the optimised excitation and detection systems.

Furthermore, the aforementioned embodiments generate a large dataset of variable fluorescence values from the interrogated volume. Because the interrogated volume is continuously exchanged from the sample 1 volume, the distribution of variable fluorescence values within this dataset is a function of cell density (the lower the cell concentration, the higher the range of values, normalised to the mean). The embodiments provide an analysis method that accurately converts the distribution data to cell concentration, from homogeneous populations of phytoplankton cells (a narrow range of values for variable fluorescence per cell).

The analysis method is less effective at converting the distribution of variable fluorescence values if the sample 1 includes a small number of cells with a high level of variable fluorescence per cell and a large number of cells with a low level of variable fluorescence per cell. Therefore, embodiments provide a method for determining the proportion of the total variable fluorescence that can be attributed to the cells with a high level of variable fluorescence per cell. The remaining variable fluorescence can be attributed to cells with a much lower variable fluorescence per cell.

Although a few exemplary embodiments have been shown and described, it will be appreciated by those skilled in the art that changes may be made in these exemplary embodiments without departing from the principles of the invention, the range of which is defined in the appended claims.

The invention claimed is:

1. A cell counting device for estimating the number of photoactive cells in a sample, the device comprising:
    a chamber for receiving the sample;
    at least one light source to generate at least one pulse of light and to emit the at least one pulse of light towards a section of the chamber, wherein the section of the chamber comprises a sub-sample of the sample;
    a light detector to receive light emitted from the sub-sample in response to receiving the at least one pulse of light and to generate an electronic signal associated with the received light; and
    a controller configured to
    estimate the number of photoactive cells in the sample by:
        calculating and storing a variable fluorescence [$F_v$] values of each sub-sample in a predetermined number of sub-samples, by estimating a minimal fluorescence [$F_o$] of the sub-sample using regression analysis of a first part of the light signal, estimating a maximal fluorescence [$F_m$] of the sub-sample using regression analysis of a second part of the light signal, and subtracting $F_o$ from $F_m$ for each sub-sample;
        calculating a mean of the stored $F_v$ values, and store a distance from the mean of each $F_v$ value to obtain a plurality of distances; and
        integrate a distribution of the plurality of distances to provide an estimate of the number of photoactive cells in the sample.

2. The cell counting device according to claim 1, wherein the at least one light source is configured to generate a plurality of pulses of light, and the light detector is configured to receive light from the sub-sample at time intervals less than the duration of each pulse of light to form a light signal, optionally wherein the at least one light source is configured to generate pulses of light having a frequency of between 10 Hz and 100 Hz and a duration of between 200 μs and 700 μs.

3. The cell counting device according to claim 1, wherein the controller is configured to estimate the cell density of the sample by dividing the estimate of the number of cells by a volume of the sample, and wherein the controller is configured to perform an action if the estimated cell density is greater than a first cell density threshold.

4. The cell counting device according to claim 3, further comprising a means for indicating to the user that the estimated cell density exceeds the first cell density threshold, wherein the action comprises controlling the indicating means, optionally wherein the indicating means comprises at least one of a display, an alarm and an indicator light.

5. The cell counting device according to claim 1, wherein the cell counting device is coupled to a ballast water treatment system, and the controller is configured to perform an action comprising controlling the ballast water treatment system to eliminate live cells, or wherein the cell counting device is coupled to an external display device, and the controller is configured to perform an action comprising controlling the external display device to display a message.

6. The cell counting device according to claim 1, further comprising an outlet in fluid communication with the chamber for draining the sample from the chamber, further comprising an inlet in fluid communication with the chamber, arranged such that water can continuously flow from the inlet, through the chamber, to the outlet in a first mode of operation, wherein the chamber comprises a removable blocking member for blocking the inlet or the outlet to allow a discrete sample to be measured in a second mode of operation, optionally further comprising a valve arranged in at least one of the inlet or the outlet operable to allow the cell counting device to alternate between the first mode of operation and the second mode of operation, wherein in the first mode of operation the valve is open, and in the second mode of operation the valve is closed.

7. The cell counting device according to claim 6, wherein the controller is configured to calculate the variable fluorescence of the sub-sample while the cell counting device operates in the first mode of operation, and if the variable fluorescence is less than a first $F_v$ threshold and is greater than a second $F_v$ threshold being less than the first $F_v$ threshold, the controller is configured to close the valve and to switch the cell counting device to operate in the second mode of operation, optionally wherein if the estimated cell density exceeds a second cell density threshold less than the first cell density threshold, the controller is configured to switch the cell counting device to the first mode of operation from the second mode of operation, and increase a frequency at which the variable fluorescence of the sub-samples are calculated.

8. The cell counting device according to claim 1, further comprising a stirrer configured to stir the sample, such that each sub-sample is exchanged with the sample.

9. The cell counting device according to claim 1, wherein the cells are biological fluorophores, wherein the sample is ballast water, and the cells are phytoplankton.

10. The cell counting device according to claim 1, wherein the cells comprise a photoactive organic dye.

11. The cell counting device according to claim 1, wherein a volume of each sub-sample is between 0.5% and 50% of the sample volume.

12. A system comprising:
a ballast water treatment system; and
the cell counting device according to claim 1,
wherein the controller of the cell counting device is configured to estimate a cell density of the sample by dividing the estimate of the number of cells by a volume of the sample and to control the ballast water treatment system to activate a means for eliminating live cells if the estimated cell density exceeds a cell density threshold.

* * * * *